US008684189B2

(12) United States Patent
Chen et al.

(10) Patent No.: US 8,684,189 B2

(45) Date of Patent: Apr. 1, 2014

(54) MULTIFUNCTIONAL ELECTROPROCESSED MEMBRANES

(75) Inventors: Liang Chen, Cambridge, MA (US); Lev E. Bromberg, Swampscott, MA (US); Trevor Alan Hatton, Sudbury, MA (US); Gregory C. Rutledge, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 346 days.

(21) Appl. No.: 12/840,916

(22) Filed: Jul. 21, 2010

(65) Prior Publication Data

US 2011/0174720 A1 Jul. 21, 2011

Related U.S. Application Data

(60) Provisional application No. 61/227,746, filed on Jul. 22, 2009.

(51) Int. Cl.

| | |
|---|---|
| ***B01D 71/72*** | (2006.01) |
| ***B01D 39/16*** | (2006.01) |
| ***B01D 69/12*** | (2006.01) |
| ***B32B 27/12*** | (2006.01) |
| ***B32B 27/28*** | (2006.01) |
| ***A62B 7/10*** | (2006.01) |

(52) U.S. Cl.

USPC ... 210/501; 210/500.27; 210/508; 210/502.1; 442/122; 442/123; 96/12; 96/6; 55/524; 55/528

(58) Field of Classification Search

USPC .................... 96/9, 11, 12, 13, 14, 6, 4; 95/45; 588/299, 401, 402, 249.5; 442/43, 45, 442/46, 49, 58, 63, 66, 76–77, 121–123; 210/323.1, 500.27, 500.29, 500.3, 210/500.33, 500.35, 500.42, 644, 649, 650, 210/651, 652, 653, 654, 500.1, 500.21, 210/500.24, 500.28, 501, 502.1, 503, 504, 210/506, 507, 508, 510.1; 55/527–528, 524

See application file for complete search history.

(56) References Cited

U.S. PATENT DOCUMENTS 4,650,506 A * 3/1987 Barris et al. .................... 55/487
7,445,799 B1 11/2008 Sarangapani et al.

(Continued)

FOREIGN PATENT DOCUMENTS

WO WO-2009/064767 A2 5/2009

OTHER PUBLICATIONS

Bromberg et al., Poly(N-vinylguanidine): Characterization, and catalytic and bactericidal properties, Nov. 1, 2007, Polymer, 48, pp. 7490-7498.*

(Continued)

*Primary Examiner* — David C Mellon

(74) *Attorney, Agent, or Firm* — Alan W. Steele; Foley Hoag LLP

(57) ABSTRACT

Described is the application of layer-by-layer (LbL) electrostatic assembly techniques to electrospun nanofibers in order to fabricate novel, breathable electrospun fiber-based chemical and biological detoxifying protective fabrics and filters. The combination of layer-by-layer electrostatic assembly and electrospinning technique allows one to take advantage of high specific surface area, light weight and breathability of electrospun fiber mats while simultaneously providing the versatility to incorporate different functional polyelectrolytes to achieve multifunctional coatings for both chemical and biological protection together. The functionalized fiber mats can be incorporated into breathable chemical and biological protective fabrics, filters and masks. In addition, LbL electrostatic coating of porous non-woven materials provides the versatility to generate multifunctional polymer-based membrane materials for other applications.

20 Claims, 16 Drawing Sheets

(56) References Cited

U.S. PATENT DOCUMENTS

2006/0234573 A1* 10/2006 Rock .............................. 442/59
2010/0319113 A1* 12/2010 Rock et al. ........................ 2/457

OTHER PUBLICATIONS

Ding et al., Preparation and characterization of self-assembled polyelectrolyte multilayered films on electrospun nanofibers, 2005, Thin Solid films, Elsevier, 491, pp. 23-28.*

Ge et al, The fabrication of hollow multilayered polyelectrolyte fibrous mats and its morphology study, Aug. 12, 2006, Colloids and Surfaces A: Physicochem Eng. Aspects, 293, pp. 272-277.*

Bromberg, L. et al., "Degradation of Chemical Warfare Agents by Reactive Polymers", *Ind. Eng. Chem. Res.*, 48:1650-1659 (American Chemical Society, 2009).

Chen, L., "Next Generation of Electrospun Textiles for Chemical and Biological Protection and Air Filtration", Mass. Inst. of Tech., Jul. 23, 2009 (Abstract).

Chen, L. et al., "Chemical protection fabrics via surface oximation of electrospun polyacrylonitrile fiber mats", *J. Mater. Chem.*, 19:2432-2438 (Royal Society of Chemistry, 2009).

Chen, L. et al., "Electrospun cellulose acetate fibers containing chlorohexidine as a bactericide", *Polymer*, 49:1266-1275 (Elsevier Ltd. 2008).

Chen, L. et al., "Multifunctional Electrospun Fabrics via Layer-by-Layer Electrostatic Assembly for Chemical and Biological Protection", *Chem. Mater.*, 22:1429-1436 (American Chemical Society, 2010).

Graham, K. et al., "Incorporation of Electrospun Nanofibers Into Functional Structures", *INJ*, 21-24 (2004).

Krogman, K. C. et al., "Spraying asymmetry into functional membranes Layer-by-Layer", *Nature Materials*, 1-7 (Macmillan Publishers Ltd., 2009).

International Search Report and Written Opinion of the International Searching Authority from corresponding PCT patent application No. PCT/US2010/042762 filed Jul. 21, 2010.

Decher, G., Fuzzy nanoassemblies: Toward layered polymeric multicomposites. *Science* 277:1232-1237 (1997).

Gaetjens, E. et al., Intramolecular carboxylate attack on ester groups. The hydrolysis of substituted phenyl acid succinates and phenyl acid glutarates. *J. Am. Chem. Soc.* 82:5328-5335 (1960).

* cited by examiner

Octanedioic acid hydroxyamide isopropenyl-amide

N-hydroxyacrylamide

2-Ethyl-2-hexyl-hex-5-enoic acid hydroxyamide

*N*-[(Hydroxy-methyl-carbamoyl)-methyl]-
2-methyl-acrylamide

MULTIFUNCTIONAL ELECTROPROCESSED MEMBRANES

RELATED APPLICATIONS

This application claims the benefit of priority to U.S. Provisional Patent Application Ser. No. 61/227,746, filed Jul. 22, 2009; the content of which is hereby incorporated by reference.

GOVERNMENT SUPPORT

This invention was made with government support under Contract No. W911NF-07-1-0139, awarded by the Army Research Office. The government has certain rights in this invention.

BACKGROUND

Increasing concern over exposure to pesticides, nerve agents, and chemical and biological pollutants, along with more-frequent chemical and biological threats due to intentional or accidental release of toxic agents, necessitates the development of countermeasures that provide effective protection for military personnel and emergency responders. Currently, protective clothing systems, such as hazardous material (HAZMAT) suits or joint service lightweight integrated suit technology (JSLIST), are widely used to achieve full protection. These protective systems are based upon either full barrier protection through blocking contaminant permeation, or air-permeable adsorptive protective overgarments in which all the toxins are adsorbed on contact [Schreuder-Gibson, H. L.; Truong, Q.; Walker, J. E.; Owens, J. R.; Wander, J. D.; Jones, W. E. *MRS Bulletin* 2003, 28, 574]. High thermal loads from poor water-vapor-permeability and excess insulation as well as the weight and bulkiness of these protective fabrics and suits impair the wearer's performance. Recently, protective fabrics have been developed based on selectively-permeable membranes, which allow for permeation of water vapor while remaining resistant to the permeation of organic molecules [Wilusz, E.; Truong Q. T.; Rivin, D.; Kendrick, C. E. *Polym. Mat. Sci. Eng.* 1997, 77, 365]. The new generation of protective fabrics is envisioned not only to absorb or block toxic chemical and biological agents but also to detoxify them to reduce the risk of secondary contamination [Schreuder-Gibson, H. L.; Truong, Q.; Walker, J. E.; Owens, J. R.; Wander, J. D.; Jones, W. E. *MRS Bulletin* 2003, 28, 574].

Electrospinning is a fiber-forming process that employs electrostatic forces to stretch a jet of polymer solution or melt, producing continuous fibers with diameters ranging from micrometers down to several nanometers [Dzenis, Y. *Science* 2004, 304, 1917; Rutledge, G. C.; Fridrikh, S. V. *Adv. Drug Delivery Rev.* 2007, 59, 1384; Reneker, D. H.; Yarin, A. L. *Polymer* 2008, 49, 2387; Reneker, D. H.; Chun, I. *Nanotechnology* 1996, 7, 216; Greiner, A.; Wendorff, J. H. *Angew. Chem. Int. Ed.* 2007, 46, 5670; Li, D.; Xia, Y. *Adv. Mater.* 2004, 16, 1151; Ramakrishna, S.; Fujihara, K.; Teo, W. E.; Yong, Y.; Ma. Z. W.; Ramaseshan, R. *Materials Today* 2006, 9, 40; and Ramakrishna, S.; Fujihara, K.; Teo, W.-E.; Lim, T.-C.; Ma. Z. An Introduction to Electrospinning and Nanofibers, World Scientific Publishing Company: Singapore, 2005]. Electrospun nanofibers attract great interest in the materials science community due to their ease of processing, ease of functionalization, high surface area, light weight, breathability and flexibility. Electrospun nanofibers for chemical and biological protection are well-represented in the art [U.S. Pat. No. 7,445,799 (Sarangapani), hereby incorporated by reference in its entirety; and K. Graham, M. Goggins, H. Schreuder-Gibson, "Incorporation of Electrospun Nanofibers Into Functional Structures," Presented at INTC 2003, sponsored by INDA, Association of the Nonwoven Fabrics Industry and TAPPI, Technical Association of the Pulp & Paper Industry, Sep. 15-18, 2003, Baltimore, Md.]. The ease of implementation as well as the remarkable properties of electrospun fiber mats, such as small fiber size, high specific surface area, high porosity and low fabric weight, have inspired the use of the electrospun fiber mats in a broad range of applications, including scaffolds in tissue engineering, composite materials, filters, sensors and energy storage devices [Ma, Z. W.; Kotaki, M.; Inai, R.; Ramakrishna, S. *Tissue Eng.* 2005, 11, 101; Roso, M.; Sundarrajan, S.; Pliszka, D.; Ramakrishna, S.; Modesti, M. *Nanotechnology* 2008, 19, 285707/1-285707/6; Yoon, K.; Hsiao, B. S.; Chu, B. J. Mater. Chem. 2008, 18, 5326; Thavasi, V.; Singh, G.; Ramakrishna, S. *Energy Environ. Sci.* 2008, 1, 205; and Kim, I. D.; Rothschild, A.; Lee, B. H.; Kim, D. Y.; Jo, S. M.; Tuller, H. L. *Nano Lett.* 2006, 6, 2009]. The potential for application of electrospun fiber mats in protective clothing was demonstrated by Schreuder-Gibson and coworkers [Gibson, P.; Schreuder-Gibson, H. L.; Rivin, D. *Colloids Surf. A* 2001, 187-188, 469; Gibson, P. W.; Schreuder-Gibson, H. L.; Rivin, D. *AICHE Journal* 1999, 45, 190; and Gibson, H. L.; Gibson, P.; Senecal, K.; Sennett, M.; Walker, J.; Yeomans, W.; Ziegler, D.; Tsai, P. P. *J. Adv. Mater.* 2002, 34, 44]. They showed that lightweight electrospun fabrics exhibit higher breathability than do barrier materials while displaying better airflow resistance and enhanced aerosol particle retention compared to current commercially available membranes. "Breathability" in this instance is defined as transmission of water vapor but not liquid water.

Breathable porous membranes such as Celgard® 2400, PAN/PET (a polyethyleneterephthalate fleece coated with a thin layer of polyacrylonitrile) and Isopore™ (an etched ion-track polycarbonate membrane) coated by alternating electrostatic adsorption of cationic and anionic compounds (polyelectrolytes and bolaamphiphiles) are known in the art [F. Van Ackern, L. Krasermann, B. Tieke, "Ultrathin membranes for gas separation and pervaporation prepared upon electrostatic self-assembly of polyelectrolytes," *Thin Solid Films* 1998, 327-29, 762-766; and the International Conference on Organized Molecular Films No. 8, held in Pacific Grove, Calif., on Aug. 24, 1997], but they are not based on electrospun nanofibers.

However, Obendorf et al. showed that laminated fabrics with electrospun polypropylene fiber layers significantly limit the penetration of liquid pesticides while still maintaining good water vapor permeability [Lee, S.; Obendorf, S. K. *J. Appl. Polym. Sci.* 2006, 102, 3430]. The combination of high breathability and efficient barrier properties of electrospun fabrics makes them promising candidates for the next generation of protective clothing. Moreover, the high specific surface areas of electrospun fiber mats allow attachment of functional compounds to obtain chemical or biological detoxifying protective clothing. Ramakrishna et al. successfully electrospun fibers with a reactive compound, (3-carboxy-4-iodosobenzyl)oxy-β-cyclodextrin, and showed that these reactive fabrics can decompose paraoxon, an organophosphate pesticide [Ramaseshan, R.; Sundarrajan, S.; Liu, Y.; Barhate, R. S.; Lala, N. L.; Ramakrishna, S. *Nanotechnology* 2006, 17, 2947]. In another study, electrospun zinc titanate nanofibers were tested as reactive sorbents capable of detoxifying nerve and mustard agent simulants [Ramaseshan, R.; Ramakrishna, S. *J. Am. Ceram. Soc.* 2007, 90, 1836].

Various biocides such as silver nanoparticles, quaternary ammonium salts or their derivatives, compounds with biguanide groups, and N-halamine, have been incorporated into electrospun fiber membranes to serve as antimicrobial filters or to create a biological protective clothing [Lala, N. L.; Ramaseshan, R.; Bojun, L.; Sundarrajan, S.; Barhate, R. S.; Ying-jun, L.; Ramakrishna, S. *Biotechnol. Bioeng.* 2007, 97, 1357; Fu, G-D.; Yao, F.; Li, Z.; Li, X. *J. Mater. Chem.* 2008, 18, 859; Fan, L.; Du, Y.; Zhang, B.; Yang, J.; Zhou, J.; Kennedy, J. F. *Carbohydr. Polym.* 2006, 65, 447; Chen, L.; Bromberg, L.; Hatton, T. A.; Rutledge, G. C. *Polymer* 2008, 49, 1266; and Tan, K.; Obendorf, S. K. *J. Membr. Sci.* 2007, 305, 287].

Functionalization of electrospun nanofibers with antimicrobial functionality such as silver nanoparticles is also known in the art [N. L. Lala, R. Ramaseshan, L. Bojun, S. Sundarrajan, R. S. Barhate, L. Ying-jun, S. Ramakrishna, “Fabrication of nanofibers with antimicrobial functionality used as filters: protection against bacterial contaminants,” *Biotechnol. Bioeng.* 2007, 97 (6), 1357-1365]. However, silver nanoparticles, while being bactericidal and bacteriostatic through the action of silver ions slowly releasing into the environment, are not effective in killing a wide range of microorganisms on contact.

The use of small molecular weight, broad-range bactericides, such as chlorhexidine, for incorporation into nanofibers, either through physical enmeshment or covalent attachment, has also been disclosed [L. Chen, L. Bromberg, T. A. Hatton, G. C. Rutledge, “Electrospun cellulose acetate fibers containing chlorhexidine as a bactericide,” *Polymer* 2008, 49 (5), 1266-1275]. The resulting nanofibers are capable of killing bacteria on contact, but are unable to degrade organophosphorous esters, which are common pesticides and chemical warfare agents.

Chemical methods to counteract nerve agents and remediate organophosphate (OP) contamination by means of nanoparticles, polymers and nanofibers functionalized by α-nucleophilic agents are known [Bromberg, L.; Schreuder-Gibson, H.; Creasy, W. R.; McGarvey, D. J.; Fry, R. A.; Hatton, T. A. *Ind. Eng. Chem. Res.* 2009, 48, 1650; Bromberg, L.; Zhang, H.; Hatton, T. A. *Chem. Mater.* 2008, 20, 2001; Bromberg, L.; Hatton, T. A. *Ind. Eng. Chem. Res.* 2005, 44, 7991; Chen, L.; Bromberg, L.; Schreuder-Gibson, H.; Walker, J.; Hatton, T. A; Rutledge, G. C. *J. Mater. Chem.* 2009, 19, 2432; Chen, L.; Bromberg, L.; Hatton, T. A.; Rutledge, G. C. *Polymer* 2007, 48, 4675]. For example, fiber mats functionalized with α-nucleophilic oxime moieties were prepared by either electrospinning blends of polyacrylamidoxime (PAAO) and polyacrylonitrile (PAN) or surface oximation of prefabricated PAN fiber mats, and demonstrated to possess a pronounced capability to hydrolyze chemical nerve agent simulants in the presence of moisture. The fiber post-spin modification strategy has the advantages of higher surface density of oxime functional groups, enhanced reactivity and ease of implementation compared to the PAN/PAAO blending strategy.

Polycationic polymers, such as poly(N-vinylguanidine), are capable of both killing a broad range of bacteria and catalytically degrading organophosphate esters such as warfare agents [L. Bromberg, T. A. Hatton, “Poly(N-vinylguanidine): Characterization, and catalytic and bactericidal properties,” *Polymer* 2007, 48, 7490-7498], but are stably bound if adsorbed onto electrospun nanofibers.

Polyanionic polymers, such as poly(sodium hydroxamate)s and poly(sodium acrylamidoxime)s, are known in the art to degrade chemical warfare agents [L. Bromberg, H. Schreuder-Gibson, W. R. Creasy, D. J. McGarvey, R. A. Fry, T. A. Hatton, “Degradation of chemical warfare agents by reactive polymers,” *Ind. Eng. Chem. Res.* 2009, 48, 1650-1659], but would be separated from electrospun nanofibers if simply enmeshed, in aqueous milieu.

The layer-by-layer (LbL) electrostatic assembly technique offers another strategy of electrospun fiber surface functionalization. The LbL electrostatic assembly is a simple, versatile and inexpensive approach to generate functional multilayer thin film coatings on surfaces [Hammond, P. T. *Adv. Mater.* 2004, 16, 1271; Decher, G. *Science* 1997, 277, 1232]. The utilization of electrospun fiber mats as substrates for LbL-based functional coatings enhances the functioning of multi-layered coatings by significantly increasing the specific surface area of substrates [Wang, X.; Kim, Y-G.; Drew, C.; Ku, B-C.; Kumar, J.; Samuelson, L. A. *Nano Lett.* 2004, 4, 331; Yang, G.; Gong, J.; Yang, R.; Guo, H.; Wang, Y.; Liu, B.; Dong, S. *Electrochem. Commun.* 2006, 8, 790; Lee, J. A.; Krogman, K. C.; Ma, M.; Hill, R. M.; Hammond, P. T.; Rutledge, G. C. *Adv. Mater.* 2009, 21, 1252; and Krogman, K. C.; Lowery, J. L.; Zacharia, N. S.; Rutledge, G. C.; Hammond, P. T. *Nat. Mater.* 2009, 8, 512]. Wang et al. showed that a fluorescent probe LbL-assembled onto electrospun cellulose acetate membranes resulted in a dramatic increase in sensitivity of optical sensors. For the application in protective fabrics, Lee et al. demonstrated that electrospun fibers used as the substrate for titanium dioxide nanoparticle coatings increased the substrate surface area by $10^4$ times compared to the flat film, which enhanced photo-catalytic decomposition of toxic industrial chemicals. In addition, Krogman et al. employed a newly-developed spray-assisted LbL assembly technique to functionalize electrospun nylon fibers with titanium dioxide nanoparticles for protective fabrics, in which they could obtain conformal coatings or bridge the surface voids by controlling the spraying conditions; in this regard, they could achieve LbL-functionalized fiber mats with improved photo-catalytic capability without sacrificing water vapor permeability or breathability of the electrospun fiber mats.

SUMMARY

Certain aspects of the invention relate to materials, such as electrospun nanofibers and membranes formed therefrom, which may be used for chemical and biological protection. In certain embodiments, the invention relates to an electrospun nanofiber or membrane modified by polyelectrolyte complexes via electrostatic assembly. In certain embodiments, the modified electrospun nanofiber or membrane possesses sufficient porosity to enable high breathability. In certain embodiments, the modified electrospun nanofiber or membrane is capable of killing bacteria on contact and capable of degrading organophosphorous esters.

One aspect of the invention relates to a membrane comprising a plurality of polymer-coated electroprocessed nanofibers, wherein said polymer coating comprises at least one polyelectrolyte bilayer, said bilayer comprises a plurality of polycations in a polycationic layer and a plurality of polyanions in a polyanionic layer, at least one of said polycations is antimicrobial, and at least one of said polyanions is esterolytic.

In certain embodiments, the present invention relates to any one of the aforementioned membranes, wherein the electroprocessed nanofibers are electrospun.

In certain embodiments, the present invention relates to any one of the aforementioned membranes, wherein the plurality of electroprocessed nanofibers are oriented in a substantially uniform direction in a plane.

In certain embodiments, the present invention relates to any one of the aforementioned membranes, wherein the plurality of electroprocessed nanofibers are randomly oriented in a plane.

In certain embodiments, the present invention relates to any one of the aforementioned membranes, wherein the membrane has a surface area of between about 0.1 $m^2/g$ and about 1000 $m^2/g$.

In certain embodiments, the present invention relates to any one of the aforementioned membranes, wherein the electroprocessed nanofibers are homopolymers, copolymers, or a blend of polymers, selected from the group consisting of alginates, aromatic copolyesters, cellulose acetates, cellulose nitrites, collagens, ethylene-methacrylic acid copolymers, ethylene-vinyl acetate copolymers, fluoropolymers, modified celluloses, neoprenes, poly(p-xylylene), polyacrylamides, polyacrylates, polyacrylonitriles, polyamides, polyarylamides, polyarylenevinylenes, polybenzimidazoles, polybenzothiazoles, polybutadienes, polybutenes, polycarbonates, polyesters, polyether ketones, polyethers, polyethylenes, polyhydroxyethyl methacrylates, polyimides, polylactides, polylactones, polymethacrylates, polymethacrylonitriles, polymethylmethacrylates, poly-N-vinylpyrrolidones, polyolefins, polyoxazoles, polyphenylene, polypropylenes, polysilanes, polysiloxanes, polystyrenes, polysulfides, polysulfones, polytetrafluoroethylenes, polyurethanes, polyvinyl acetates, polyvinylacetate-methacrylic copolymers, polyvinylidene chlorides and unmodified celluloses.

In certain embodiments, the present invention relates to any one of the aforementioned membranes, wherein the electroprocessed nanofibers are homopolymers of acrylonitrile.

In certain embodiments, the present invention relates to any one of the aforementioned membranes, wherein the diameter of electroprocessed nanofibers are between 1 nm and 1000 nm.

In certain embodiments, the present invention relates to any one of the aforementioned membranes, wherein the number of bilayers is between 1 and about 1000.

In certain embodiments, the present invention relates to any one of the aforementioned membranes, wherein membrane exhibits pore sizes of between about 0.01 microns to about 100 microns.

In certain embodiments, the present invention relates to any one of the aforementioned membranes, wherein at least one polycation inhibits the growth of bacteria on contact.

In certain embodiments, the present invention relates to any one of the aforementioned membranes, wherein at least one polycation is a polymer comprising at least one subunit represented by

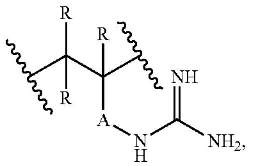

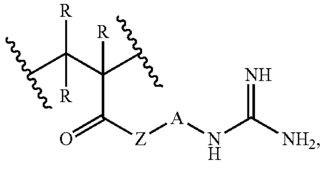

-continued

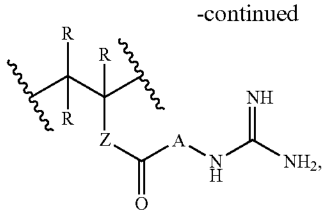

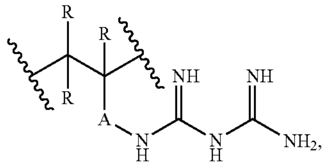

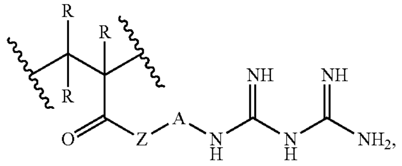

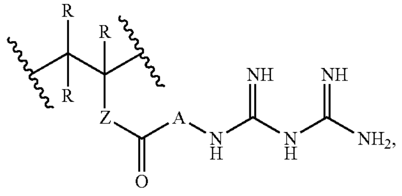

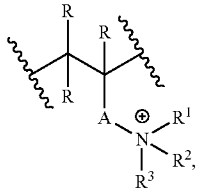

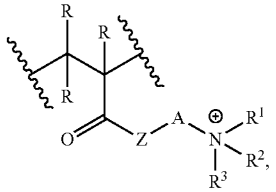

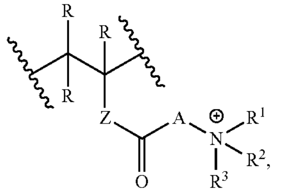

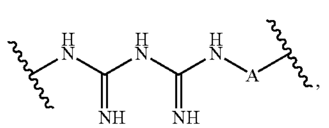

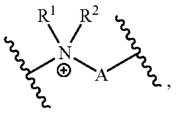

or salts thereof;

wherein, independently for each occurrence,

Z is absent, —O—, —S—, or —N(R)—;

A is absent or selected from the group consisting of alkylene, arylene, heteroarylene, alkylene-arylene, alkylene-heteroarylene, arylene-alkylene, heteroarylene-alkylene, alkylene-arylene-alkylene, and alkylene-heteroarylene-alkylene;

R is hydrogen or alkyl;

$R^1$ is hydrogen or alkyl;

$R^2$ is alkyl; and $R^3$ is alkyl.

In certain embodiments, the present invention relates to any one of the aforementioned membranes, wherein the at least one polycation is a polymer comprising at least one subunit represented by

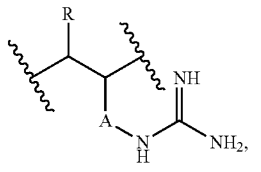

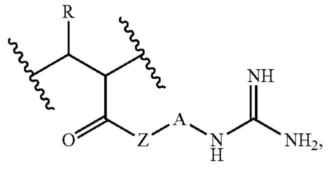

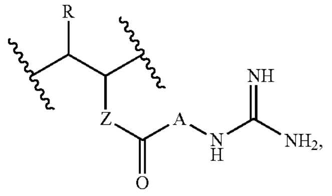

or salts thereof.

In certain embodiments, the present invention relates to any one of the aforementioned membranes, wherein the at least one polycation is a polymer comprising at least one subunit represented by

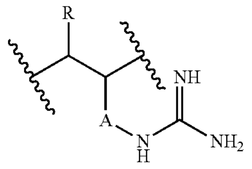

or a salt thereof.

In certain embodiments, the present invention relates to any one of the aforementioned membranes, wherein the at least one polycation is a polymer comprising at least one subunit represented by

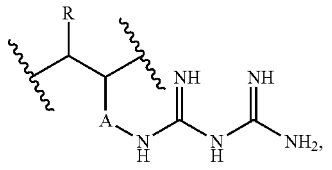

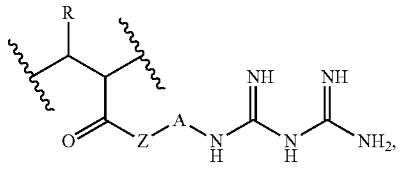

-continued

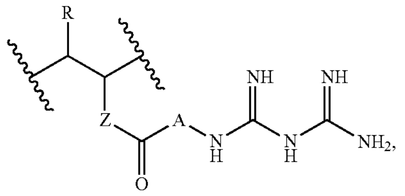

or salts thereof.

In certain embodiments, the present invention relates to any one of the aforementioned membranes, wherein the at least one polycation is a polymer comprising at least one subunit represented by

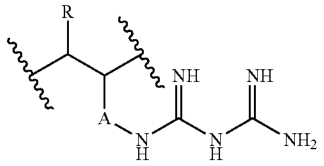

or a salt thereof.

In certain embodiments, the present invention relates to any one of the aforementioned membranes, wherein the at least one polycation is a polymer comprising at least one subunit represented by

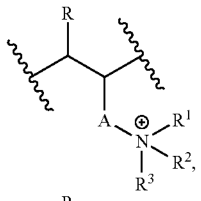

or

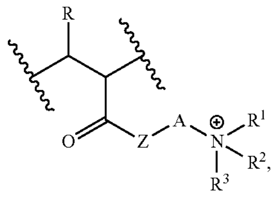

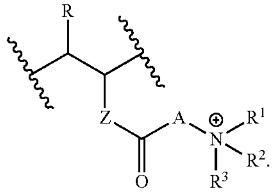

In certain embodiments, the present invention relates to any one of the aforementioned membranes, wherein the at least one polycation is a polymer comprising at least one subunit represented by

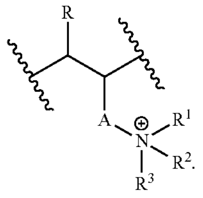

In certain embodiments, the present invention relates to any one of the aforementioned membranes, wherein the at least one polycation is a polymer comprising at least one subunit represented by

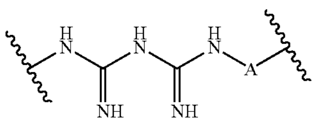

or a salt thereof.

In certain embodiments, the present invention relates to any one of the aforementioned membranes, wherein the at least one polycation is a polymer comprising at least one subunit represented by

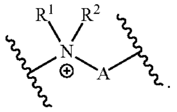

In certain embodiments, the present invention relates to any one of the aforementioned membranes, wherein Z is absent.

In certain embodiments, the present invention relates to any one of the aforementioned membranes, wherein Z is —N(R)—.

In certain embodiments, the present invention relates to any one of the aforementioned membranes, wherein Z is —N(H)—.

In certain embodiments, the present invention relates to any one of the aforementioned membranes, wherein A is alkylene, arylene, heteroarylene, alkylene-arylene, alkylene-heteroarylene, arylene-alkylene, heteroarylene-alkylene, alkylene-arylene-alkylene, and alkylene-heteroarylene-alkylene.

In certain embodiments, the present invention relates to any one of the aforementioned membranes, wherein A is absent.

In certain embodiments, the present invention relates to any one of the aforementioned membranes, wherein A is alkylene.

In certain embodiments, the present invention relates to any one of the aforementioned membranes, wherein A is hexamethylene.

In certain embodiments, the present invention relates to any one of the aforementioned membranes, wherein A is arylene.

In certain embodiments, the present invention relates to any one of the aforementioned membranes, wherein A is phenylene.

In certain embodiments, the present invention relates to any one of the aforementioned membranes, wherein R is hydrogen.

In certain embodiments, the present invention relates to any one of the aforementioned membranes, wherein R is alkyl.

In certain embodiments, the present invention relates to any one of the aforementioned membranes, wherein R is methyl.

In certain embodiments, the present invention relates to any one of the aforementioned membranes, wherein $R^1$ is hydrogen.

In certain embodiments, the present invention relates to any one of the aforementioned membranes, wherein $R^1$ is alkyl.

In certain embodiments, the present invention relates to any one of the aforementioned membranes, wherein $R^1$ is methyl.

In certain embodiments, the present invention relates to any one of the aforementioned membranes, wherein $R^2$ is methyl.

In certain embodiments, the present invention relates to any one of the aforementioned membranes, wherein $R^3$ is methyl.

In certain embodiments, the present invention relates to any one of the aforementioned membranes, wherein said plurality of polycations consists essentially of poly(N-vinylguanidine) (PVG), poly(diallyl dimethyl ammonium chloride) (PDAC), polyarginine, polyallylaminehydrochloride (PAH), linear polyethyleneimine (LPEI), branched polyethyleneimine (BPEI), poly(amidoamine) dendrimer (PAMAM), poly(N-(1,3-bis(2-ethylhexyl)-5-methylhexahydropyrimidin-5-yl)acrylamide), poly(hexamethylenebiguanide) (PHMB), or poly(hexamethylene-5-(phenylene)biguanide, or salts thereof.

In certain embodiments, the present invention relates to any one of the aforementioned membranes, wherein said plurality of polycations consists essentially of poly(N-vinylguanidine) (PVG) or a salt thereof.

In certain embodiments, the present invention relates to any one of the aforementioned membranes, wherein the plurality of polycations are polymers having degrees of polymerization of between about 3 and about 25,000 subunits.

In certain embodiments, the present invention relates to any one of the aforementioned membranes, wherein the plurality of polycations are polymers having degrees of polymerization of between about 20 and about 10,000.

In certain embodiments, the present invention relates to any one of the aforementioned membranes, wherein the plurality of polycations are polymers having degrees of polymerization of between about 100 and about 2,500.

In certain embodiments, the present invention relates to any one of the aforementioned membranes, wherein at least one polyanion degrades organophosphorous esters on contact.

In certain embodiments, the present invention relates to any one of the aforementioned membranes, wherein at least one polyanion is a polymer comprising at least one subunit represented by

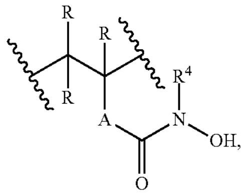

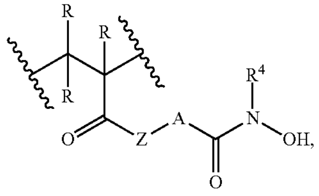

-continued

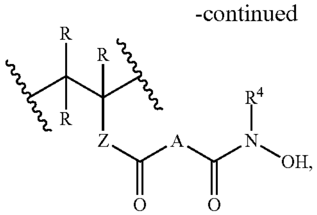

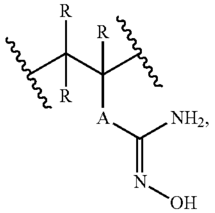

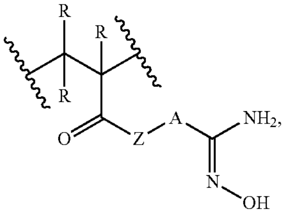

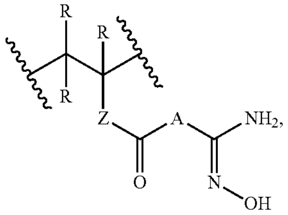

and salts thereof;

wherein, independently for each occurrence,

Z is —O—, —S—, or —N(R)—;

A is absent or selected from the group consisting of alkylene, arylene, heteroarylene, alkylene-arylene, alkylene-heteroarylene, arylene-alkylene, heteroarylene-alkylene, alkylene-arylene-alkylene, and alkylene-heteroarylene-alkylene;

R is hydrogen or alkyl; and $R^4$ is hydrogen or alkyl.

In certain embodiments, the present invention relates to any one of the aforementioned membranes, wherein the at least one polyanion is a polymer comprising at least one subunit represented by

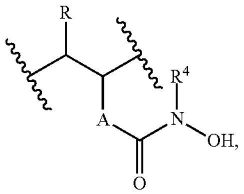

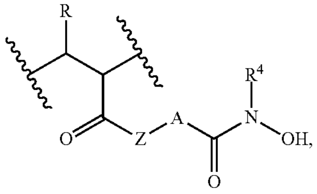

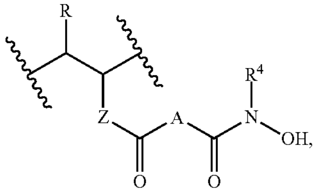

and salts thereof.

In certain embodiments, the present invention relates to any one of the aforementioned membranes, wherein the at least one polyanion is a polymer comprising at least one subunit represented by

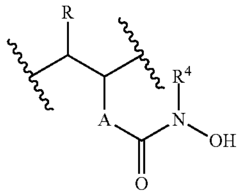

or a salt thereof.

In certain embodiments, the present invention relates to any one of the aforementioned membranes, wherein the at least one polyanion is a polymer comprising at least one subunit represented by

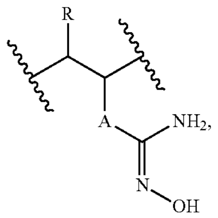

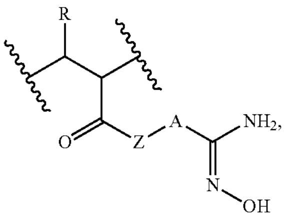

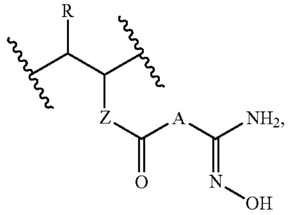

and salts thereof.

In certain embodiments, the present invention relates to any one of the aforementioned membranes, wherein the at least one polyanion is a polymer comprising at least one subunit represented by

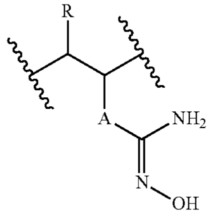

or a salt thereof.

In certain embodiments, the present invention relates to any one of the aforementioned membranes, wherein Z is absent.

In certain embodiments, the present invention relates to any one of the aforementioned membranes, wherein Z is —N(R)—.

In certain embodiments, the present invention relates to any one of the aforementioned membranes, wherein Z is —N(H)—.

In certain embodiments, the present invention relates to any one of the aforementioned membranes, wherein R is hydrogen.

In certain embodiments, the present invention relates to any one of the aforementioned membranes, wherein R is methyl.

In certain embodiments, the present invention relates to any one of the aforementioned membranes, wherein $R^4$ is hydrogen.

In certain embodiments, the present invention relates to any one of the aforementioned membranes, wherein $R^4$ is methyl.

In certain embodiments, the present invention relates to any one of the aforementioned membranes, wherein A is alkylene, arylene, heteroarylene, alkylene-arylene, alkylene-heteroarylene, arylene-alkylene, heteroarylene-alkylene, alkylene-arylene-alkylene, and alkylene-heteroarylene-alkylene.

In certain embodiments, the present invention relates to any one of the aforementioned membranes, wherein A is absent.

In certain embodiments, the present invention relates to any one of the aforementioned membranes, wherein A is alkylene.

In certain embodiments, the present invention relates to any one of the aforementioned membranes, wherein A is arylene.

In certain embodiments, the present invention relates to any one of the aforementioned membranes, wherein said plurality of polyanions consists essentially of poly(N-hydroxyacrylamide) (PHA), poly(N-hydroxyacrylamidoxamate), poly(octanedioic acid hydroxyamide ispropenylamide), poly(2-ethyl-2-hexyl-hex-5-enoic acid hydroxyamide), poly (N-[(hydroxy-methyl-carbamoyl)-methyl]-2-methyl-acrylamide, or salts thereof.

In certain embodiments, the present invention relates to any one of the aforementioned membranes, wherein said plurality of polyanions consists essentially of poly(N-hydroxyacrylamide) (PHA) or a salt thereof.

In certain embodiments, the present invention relates to any one of the aforementioned membranes, wherein the plurality of polyanions are polymers having degrees of polymerization of between about 3 and about 25,000 subunits.

In certain embodiments, the present invention relates to any one of the aforementioned membranes, wherein the plurality of polyanions are polymers having degrees of polymerization of between about 20 and about 10,000.

In certain embodiments, the present invention relates to any one of the aforementioned membranes, wherein the plurality of polyanions are polymers having degrees of polymerization of between about 100 and about 2,500.

In certain embodiments, the present invention relates to any one of the aforementioned membranes, wherein the polymer coating is conformal.

In certain embodiments, the present invention relates to any one of the aforementioned membranes, wherein the air flow resistivity of the membrane is about $1.0\times10^{13}$ l/m$^2$ to about $1.4\times10^{13}$ l/m$^2$.

In certain embodiments, the present invention relates to any one of the aforementioned membranes, wherein the water vapor diffusion resistivity of the membrane is about $1\times10^6$ s/m$^2$ to about $2\times10^6$ s/m$^2$ at a relative humidity of between about 0.3 and 0.7.

Another aspect of the invention relates to a article comprising any one of the aforementioned membranes.

In certain embodiments, the present invention relates to any one of the aforementioned articles, wherein the article is a fabric, filters, mask or article of clothing.

In certain embodiments, the present invention relates to any one of the aforementioned articles, wherein the membrane is placed between two conventional membranes.

DETAILED DESCRIPTION

Figure 1:
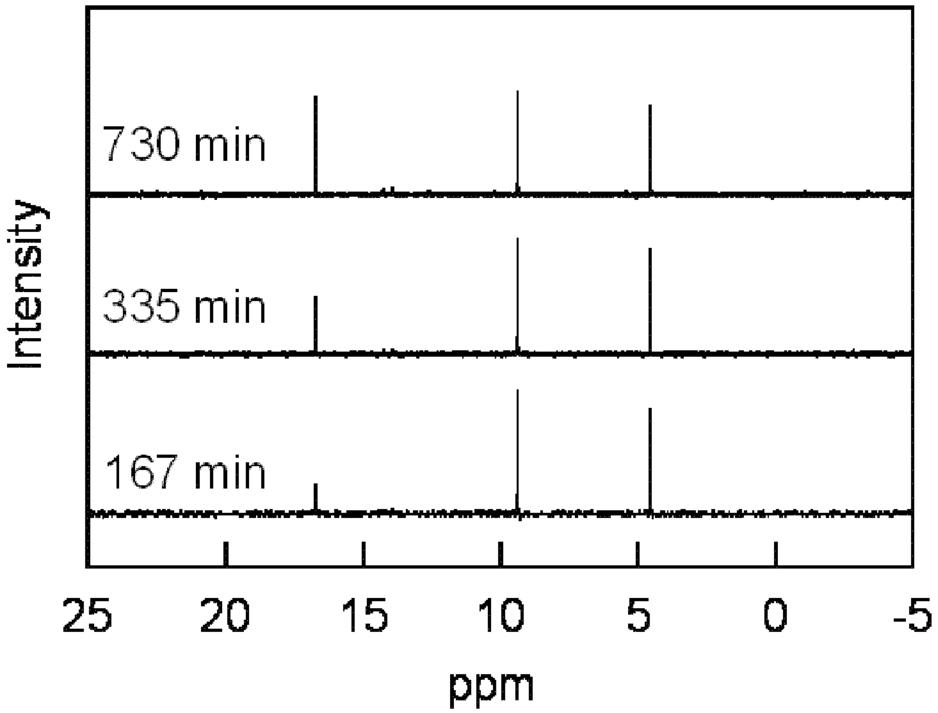
FIG. 1 depicts a time series of $^{31}$P NMR spectra of DFP degradation in aqueous solution. The conditions are as follows: $[DFP]_o$ is 5 mM; $[HA]_o$ is 10 mM; 50 mM TES buffer; the pH is 7.0; and the temperature is 25° C.

Certain aspects of the invention relates to membranes comprised of electrospun nanofibers that are rendered multifunctional by the sequential conformal deposition of polycations and polyanions on the surface of the nanofibers (i.e., the surface of the electrospun nanofibers are used as templates for ionic multilayer assembly), and methods of use thereof. In certain embodiments, bactericidal properties are achieved in such membranes through one or more components of the assembly having inherent bactericidal properties, while chemically protective capabilities in such membranes are afforded due to one or more components of the assembly possessing inherent reactivity toward organophosphate esters (esterolytic activity).

For example, a nucleophilic and chemically reactive polyanion, poly(N-hydroxyacrylamide) (PHA), and an antimicrobial polycation, poly(N-vinylguanidine) (PVG), were synthesized and assembled onto prefabricated polyacrylonitrile (PAN) fiber mats. While the description provided herein focuses on LbL deposition of such polycations and polyanions, it should be understood that any method of conformal coating, such as LbL depositions which include neutral layers, chemical vapor deposition, and dip-coating, may alternatively be used to prepare the membranes described herein. The performance of the functionalized mats in organophosphate (OP) decomposition was tested with diisopropyl fluorophosphate (DFP), a widely used simulant for G-type nerve agents [Yang, Y.-C.; Baker, J. A.; Ward, J. R. *Chem. Rev.* 1992, 92, 1729]. The antibacterial properties of these functionalized mats were examined with a Gram-negative strain of *Escherichia coli* (*E. coli*) and with a Gram-positive strain of *Staphylococcus epidermidis* (*S. epidermidis*).

DEFINITIONS

For convenience, certain terms employed in the specification, examples, and appended claims are collected here.

All definitions, as defined and used herein, should be understood to control over dictionary definitions, definitions in documents incorporated by reference, and/or ordinary meanings of the defined terms.

The indefinite articles “a” and “an,” as used herein in the specification and in the claims, unless clearly indicated to the contrary, should be understood to mean “at least one.”

The phrase “and/or,” as used herein in the specification and in the claims, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc.

As used herein in the specification and in the claims, “or” should be understood to have the same meaning as “and/or” as defined above. For example, when separating items in a list, “or” or “and/or” shall be interpreted as being inclusive, i.e., the inclusion of at least one, but also including more than one, of a number or list of elements, and, optionally, additional unlisted items. Only terms clearly indicated to the contrary, such as “only one of” or “exactly one of,” or, when used in the claims, “consisting of,” will refer to the inclusion of exactly one element of a number or list of elements. In general, the term “or” as used herein shall only be interpreted as indicating exclusive alternatives (i.e., “one or the other but not both”) when preceded by terms of exclusivity, such as “either,” “one of,” “only one of,” or “exactly one of.” “Consisting essentially of,” when used in the claims, shall have its ordinary meaning as used in the field of patent law.

As used herein in the specification and in the claims, the phrase “at least one,” in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures.

For purposes of this invention, the chemical elements are identified in accordance with the Periodic Table of the Elements, CAS version, Handbook of Chemistry and Physics, 67th Ed., 1986-87, inside cover.

The articles “a” and “an” are used herein to refer to one or to more than one (i.e., to at least one) of the grammatical object of the article. By way of example, “an element” means one element or more than one element.

The term “alkenyl” as used herein, means the radical formed by removing one hydrogen atom from a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyloxy" means an alkyl group, as defined herein, appended to the parent molecular moiety through an oxygen atom. Representative examples of alkyloxy include, but are not limited to, methoxy, ethoxy, propoxy, 2-propoxy, butoxy, tert-butoxy, pentyloxy, and hexyloxy.

The term "alkyloxycarbonyl" means an alkyloxy group, as defined herein, appended to the parent molecular moiety through a carbonyl group, represented by —C(═O)—, as defined herein. Representative examples of alkyloxycarbonyl include, but are not limited to, methoxycarbonyl, ethoxycarbonyl, and tert-butoxycarbonyl.

The term "alkyloxysulfonyl" as used herein, means an alkyloxy group, as defined herein, appended to the parent molecular moiety through a sulfonyl group, as defined herein. Representative examples of alkyloxysulfonyl include, but are not limited to, methoxysulfonyl, ethoxysulfonyl and propoxysulfonyl.

The term "arylalkyloxy" and "heteroalkyloxy" as used herein, means an aryl group or heteroaryl group, as defined herein, appended to the parent molecular moiety through an alkyloxy group, as defined herein. Representative examples of arylalkyloxy include, but are not limited to, 2-chlorophenylmethoxy, 3-trifluoromethylethoxy, and 2,3-methylmethoxy.

The term "arylalkyl" as used herein, means an aryl group, as defined herein, appended to the parent molecular moiety through an alkyl group, as defined herein. Representative examples of alkyloxyalkyl include, but are not limited to, tert-butoxymethyl, 2-ethoxyethyl, 2-methoxyethyl, and methoxymethyl.

The term "alkyl" means the radical formed by removing one hydrogen atom from a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylene" pertains to a bidentate (diradical) moiety obtained by removing two hydrogen atoms, either both from the same carbon atom, or one from each of two different carbon atoms, of a hydrocarbon compound, which may be aliphatic or alicyclic, or a combination thereof, and which may be saturated, partially unsaturated, or fully unsaturated. Examples of linear saturated $C_{1-10}$alkylene groups include, but are not limited to, $—(CH_2)_n—$ where n is an integer from 1 to 10, for example, $—CH_2—$ (methylene), $—CH_2CH_2—$ (ethylene), $—CH_2CH_2CH_2—$ (propylene), $—CH_2CH_2CH_2CH_2—$ (butylene), $—CH_2CH_2CH_2CH_2CH_2—$ (pentylene) and $—CH_2CH_2CH_2CH_2CH_2CH_2—$ (hexylene). Examples of branched saturated $C_{1-10}$alkylene groups include, but are not limited to, $—CH(CH_3)—$, $—CH(CH_3)CH_2—$, $—CH(CH_3)CH_2CH_2—$, $—CH(CH_3)CH_2CH_2CH_2—$, $—CH_2CH(CH_3)CH_2—$, $—CH_2CH(CH_3)CH_2CH_2—$, $—CH(CH_2CH_3)—$, $—CH(CH_2CH_3)CH_2—$, and $—CH_2CH(CH_2CH_3)CH_2—$. Examples of linear partially unsaturated $C_{1-10}$alkylene groups include, but are not limited to, —CH═CH— (vinylene), $—CH═CH—CH_2—$, $—CH═CH—CH_2—CH_2—$, $—CH═CH—CH_2—CH_2—CH_2—$, —CH═CH—CH═CH—, $—CH═CH—CH═CH—CH_2—$, $—CH═CH—CH═CH—CH_2—CH_2—$, $—CH═CH—CH_2—CH═CH—$, and $—CH═CH—CH_2—CH_2—CH═CH—$. Examples of branched partially unsaturated $C_{1-10}$alkylene groups include, but are not limited to, $—C(CH_3)═CH—$, $—C(CH_3)═CH—CH_2—$, and $—CH═CH—CH(CH_3)—$. Examples of alicyclic saturated $C_{1-10}$alkylene groups include, but are not limited to, cyclopentylene (e.g., cyclopent-1,3-ylene), and cyclohexylene (e.g., cyclohex-1,4-ylene). Examples of alicyclic partially unsaturated $C_{1-10}$alkylene groups include, but are not limited to, cyclopentenylene (e.g., 4-cyclopenten-1,3-ylene), and cyclohexenylene (e.g., 2-cyclohexen-1,4-ylene, 3-cyclohexen-1,2-ylene, and 2,5-cyclohexadien-1,4-ylene). Alkylene groups may be optionally substituted with alkyl groups.

In general "-enes" refer to bidentate radicals (such as alkylene described above).

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy" as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "alkynyl" as used herein, means the radical formed by removing one hydrogen atom from a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein, means —NHC(═O)—, wherein the amido group is bound to the parent molecular moiety through the nitrogen. Examples of amido include alkylamido such as $CH_3C(═O)N(H)—$ and $CH_3CH_2C(═O)N(H)—$.

The term "amino" as used herein, refers to radicals of both unsubstituted and substituted amines appended to the parent molecular moiety through a nitrogen atom. The substituents are each independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "aryl," as used herein, means a phenyl group or a naphthyl group. The aryl groups of the present invention can be optionally substituted with one, two, three, four, or five substituents independently selected from the group consisting of alkenyl, alkyloxy, alkyloxycarbonyl, alkyloxysulfonyl, alkyl, alkylcarbonyl, alkylcarbonyloxy, alkylsulfonyl, alkylthio, alkynyl, amido, amino, carboxy, cyano, formyl, halo, haloalkyloxy, haloalkyl, hydroxyl, hydroxyalkyl, mercapto, nitro, silyl and silyloxy.

The term "arylene," is art-recognized, and as used herein, pertains to a bidentate moiety obtained by removing two hydrogen atoms of an aryl ring, as defined above.

The term "arylalkyl" or "aralkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkyloxy" or "arylalkyloxy" as used herein, means an arylalkyl group, as defined herein, appended to the parent molecular moiety through an oxygen. The term "heteroarylalkyloxy" as used herein, means an heteroarylalkyl group, as defined herein, appended to the parent molecular moiety through an oxygen.

The term "arylalkylthio" as used herein, means an arylalkyl group, as defined herein, appended to the parent molecular moiety through an sulfur. The term "heteroarylalkylthio" as used herein, means an heteroarylalkyl group, as defined herein, appended to the parent molecular moiety through an sulfur.

The term "arylalkenyl" as used herein, means an aryl group, as defined herein, appended to the parent molecular moiety through an alkenyl group. A representative example is phenylethylenyl.

The term "arylalkynyl" as used herein, means an aryl group, as defined herein, appended to the parent molecular moiety through an alkynyl group. A representative example is phenylethynyl.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "aryloxy" as used herein, means an aryl group, as defined herein, appended to the parent molecular moiety through an oxygen. The term "heteroaryloxy" as used herein, means a heteroaryl group, as defined herein, appended to the parent molecular moiety through an oxygen.

The term "carbonyl" as used herein, means a —C(═O)— group.

The term "carboxy" as used herein, means a $—CO_2H$ group.

The term "cycloalkyl" as used herein, means the radical formed by removing one hydrogen atom from a monocyclic or a multicyclic (e.g., bicyclic, tricyclic, etc.) hydrocarbon containing from 3 to 12 carbon atoms that is completely saturated or has one or more unsaturated bonds but does not amount to an aromatic group. Examples of a cycloalkyl group include cyclopropyl, cyclobutyl, cyclopentyl, cyclopentenyl, cyclohexyl and cyclohexenyl.

The term "cycloalkyloxy" as used herein, means a cycloalkyl group, as defined herein, appended to the parent molecular moiety through an oxygen.

The term "cyano" as used herein, means a —CN group.

The term "formyl" as used herein, means a —C(═O)H group.

The term "halo" or "halogen" means —Cl, —Br, —I or —F.

The term "haloalkyloxy" as used herein, means at least one halogen, as defined herein, appended to the parent molecular moiety through an alkyloxy group, as defined herein. Representative examples of haloalkyloxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl," as used herein, refers to the radical formed by removing a hydrogen atom from a non-aromatic ring system, including, but not limited to, monocyclic, bicyclic and tricyclic rings, which can be completely saturated or which can contain one or more units of unsaturation (for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, or 3 substituents independently selected from alkenyl, alkyloxy, alkyloxycarbonyl, alkyloxysulfonyl, alkyl, alkylcarbonyl, alkylcarbonyloxy, alkylsulfonyl, alkylthio, alkynyl, amido, amino, carboxy, cyano, formyl, halo, haloalkyloxy, haloalkyl, hydroxyl, hydroxyalkyl, mercapto, nitro, silyl and silyloxy. Radicals wherein 1, 2, or 3 of the carbon atoms in the heterocyclyl ring (e.g., $—CH_2—$ and —C(H)═), as defined above, can be replaced with —C(═O)— and the resulting radical is also heterocyclyl.

The term "heteroaryl" as used herein, refers to the radical formed by removing a hydrogen from an aromatic ring systems, such as, but not limited to, monocyclic, bicyclic and tricyclic rings, that have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, or 3 substituents independently selected from alkenyl, alkyloxy, alkyloxycarbonyl, alkyloxysulfonyl, alkyl, alkylcarbonyl, alkylcarbonyloxy, alkylsulfonyl, alkylthio, alkynyl, amido, amino, carboxy, cyano, formyl, halo, haloalkyloxy, haloalkyl, hydroxyl, hydroxyalkyl, mercapto, nitro, silyl and silyloxy.

The term "heteroarylene," is art-recognized, and as used herein, pertains to a bidentate moiety obtained by removing two hydrogen atoms of a heteroaryl ring, as defined above.

The term "heteroarylalkyl" or "heteroaralkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —$NO_2$ group.

The term "silyl" as used herein includes hydrocarbyl derivatives of the silyl ($H_3Si$—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, which is appended to the parent molecule through an oxygen atom.

The term "silylenes" refers to chemical compounds containing a divalent and dicoordinate silicon atom without any electrical charge.

As used herein, the term "polymer" means a molecule, formed by the chemical union of two or more subunits. The chemical subunits are normally linked together by covalent linkages. The two or more combining subunits in a polymer can be all the same, in which case the polymer is referred to as a homopolymer. They can be also be different and, thus, the polymer will be a combination of the different subunits; such polymers are referred to as copolymers.

As used herein, the "main chain" of a polymer, or the "backbone" of the polymer, is the series of bonded atoms that together create the continuous chain of the molecule. As used herein, a "side chain" of a polymer is the series of bonded atoms which are pendent from the main chain of a polymer.

The terms "cationic polyelectrolyte" or "polycation," as used interchangeably herein, refer to a polymer molecule with multiple cationic sites or moieties which are covalently bonded to the polymer and are part of the polymer molecular structure, and that said cationic sites or moieties are located either in the main-chain of the polymer, or in side-groups of the polymer.

The terms "anionic polyelectrolyte" or "polyanion," as used interchangeably herein, refer to a polymer molecule with multiple anionic sites or moieties which are covalently bonded to the polymer and are part of the polymer molecular structure, and that said anionic sites or moieties are located either in the main-chain of the polymer, or in side-groups of the polymer.

"Net cationic charge excess" is defined as the sum of all the cationic charges in a given molecule minus the sum of all negative charges in the same molecule, not including the charges of any associated counterions (such as chloride ions) which are not covalently bonded to the polymeric molecule, and shall be considered to be a positive number equal to or greater than three, for the purposes of this invention.

"Net anionic charge excess" is defined as the sum of all the anionic charges in a given molecule minus the sum of all positive charges in the same molecule, not including the charges of any associated counterions (such as sodium ions) which are not covalently bonded to the polymeric molecule, and shall be considered to be a negative number equal to or greater than three, for the purposes of this invention.

The term "bilayer" is employed herein in a broad sense and is intended to encompass, a coating structure formed by alternatively applying, in no particular order, one layer of a first charged polymeric material and one layer of a non-charged polymeric material or a second charged polymeric material. It should be understood that the layers of the first charged polymeric material and the non-charged polymeric material (or second charged polymeric material) may be intertwined with each other in the bilayer.

A material is "breathable" when it allows inert vapors and water vapor to pass through (e.g., so that perspiration can evaporate).

A material is "wind resistant" when it has a low convective transport.

The term "microorganism" or "microbe" is meant to include any organism comprised of the phylogenetic domains bacteria and archaea, as well as unicellular and filamentous fungi (such as yeasts and molds), unicellular and filamentous algae, unicellular and multicellular parasites, and viruses.

The term "antimicrobial" or "biocidal," as used interchangeably herein, means having to do with the killing, growth inhibition or growth prevention of microorganisms.

The term "growth inhibition" means reduced growth of the microorganisms.

The term "growth prevention" means that growth is stopped.

By "inherently antimicrobial" or "inherently biocidal" is meant a property of a material wherein said material would exhibit antimicrobial activity or properties in the absence of any antimicrobial activity or properties contributed by agents, compounds, or additives which are not integral to the material, not chemically bonded to the material, or detachable from the material, or after the removal or depletion of such agents, compounds, or additives from the material. "Inherently antimicrobial" or "inherently biocidal" does not mean that the material contains no leachable agents with antimicrobial activity.

The term "esterolytic" as used herein applies to material capable of enhancing or catalyzing the splitting of an ester into its component alcohol and acid. In certain embodiments, esterolytic polymers of the present invention enhance esterolysis of phosphoric esters and phosphonic esters.

An "effective amount" refers to an amount effective to kill, inhibit or prevent the growth of microorganisms and/or an amount effective the hydrolyze an ester into its component alcohol and acid.

The term "degree of polymerization" as used herein refers to the number of monomeric units in a polycation or polyanion.

Electrospinning

In the present invention, electrospinning is a form of electroprocessing (see, for example, U.S. Patent Application Publication No. 2006/0263417, hereby incorporated by reference). The term "electroprocessing" shall be defined broadly to include all methods of electrospinning, electrospraying, electroaerosoling, and electrosputtering of materials, combinations of two or more such methods, and any other method wherein materials are streamed, sprayed, sputtered or dripped across an electric field and toward a target. The electroprocessed material can be electroprocessed from one or more grounded reservoirs in the direction of a charged substrate or from charged reservoirs toward a grounded target. "Electrospinning" means a process in which fibers are formed from a solution or melt by streaming an electrically charged solution or melt through an orifice. "Electroaerosoling" means a process in which droplets are formed from a solution or melt by streaming an electrically charged polymer solution or melt through an orifice. The term electroprocessing is not limited to the specific examples set forth herein, and it includes any means of using an electrical field for depositing a material on a target.

Electrospinning is an attractive process for fabricating fibers due to the simplicity of the process and the ability to generate microscale and nanoscale features with synthetic and natural polymers [Nair L S, Bhattacharyya S, Laurencin C T. *Expert Opin Biol Ther.* 2004, 4, 659-68]. Electrospinning uses an electrical charge to form fibers. Electrospinning shares characteristics of both the commercial electrospray technique and the commercial spinning of fibers. The standard setup for electrospinning consists of a spinneret with a metallic needle, a syringe pump, a high-voltage power supply, and a grounded collector. A polymer, sol-gel, composite solution (or melt) is loaded into the syringe and this liquid is driven to the needle tip by a syringe pump, forming a droplet at the tip. When a voltage is applied to the needle, the droplet is first stretched into a structure called the Taylor cone. If the viscosity of the material is sufficiently high, varicose breakup does not occur (if it does, droplets are electrosprayed) and an electrified liquid jet is formed. The jet is then elongated and whipped continuously by electrostatic repulsion until it is deposited on the grounded collector. Whipping due to a bending instability in the electrified jet and concomitant evaporation of solvent (and, in some cases reaction of the materials in the jet with the environment) allow this jet to be stretched to nanometer-scale diameters. The elongation by bending instability results in the fabrication of uniform fibers with nanometer-scale diameters.

In principle, any electrospun material, including those that may dissolve or decompose upon exposure to certain solvents or high temperatures, may be used.

In certain embodiments, the electrospun fiber comprises a homopolymer, a copolymer or a blend of polymers selected from the group consisting of alginates, aromatic copolyesters, cellulose acetates, cellulose nitrites, collagens, ethylene-methacrylic acid copolymers, ethylene-vinyl acetate copolymers, fluoropolymers, modified celluloses, neoprenes, poly(p-xylylene), polyacrylamides, polyacrylates, polyacrylonitriles, polyamides, polyarylamides, polyarylenevinylenes, polybenzimidazoles, polybenzothiazoles, polybutadienes, polybutenes, polycarbonates, polyesters, polyether ketones, polyethers, polyethylenes, polyhydroxyethyl methacrylates, polyimides, polylactides, polylactones, polymethacrylates, polymethacrylonitriles, polymethylmethacrylates, poly-N-vinylpyrrolidones, polyolefins, polyoxazoles, polyphenylene, polypropylenes, polysilanes, polysiloxanes, polystyrenes, polysulfides, polysulfones, polytetrafluoroethylenes, polyurethanes, polyvinyl acetates, polyvinylacetate-methacrylic copolymers, polyvinylidene chlorides and unmodified celluloses. In certain embodiments, the electrospun fiber comprises polyacrylonitrile (PAN).

In certain embodiments of the invention, the diameter of the electrospun fiber is between about 1 nm and about 1000 nm. In certain embodiments, the diameter of the electrospun fiber is between about 1 nm and about 500 nm. In certain embodiments, the diameter of the electrospun fiber is between about 500 nm and about 1000 nm. In certain embodiments, the diameter of the electrospun fiber is between about 100 nm and about 200 nm. In certain embodiments, the diameter of the electrospun fiber is between about 200 nm and about 300 nm. In certain embodiments, the diameter of the electrospun fiber is between about 300 nm and about 400 nm. In certain embodiments, the diameter of the electrospun fiber is between about 400 nm and about 500 nm. In certain embodiments, the diameter of the electrospun fiber is between about 500 nm and about 600 nm. In certain embodiments, the diameter of the electrospun fiber is between about 600 nm and about 700 nm. In certain embodiments, the diameter of the electrospun fiber is between about 700 nm and about 800 nm. In certain embodiments, the diameter of the electrospun fiber is between about 800 nm and about 900 nm. In certain embodiments, the diameter of the electrospun fiber is between about 900 nm and about 100 nm.

In one embodiment the aforementioned electrospun fiber may have beads (i.e., non-uniformities in the diameter along the length of a fiber). In one embodiment of the invention, the average diameter of a bead is between about 500 nm and about 10000 nm. In one embodiment of the invention, the average diameter of a bead is between about 500 nm and about 1000 nm. In one embodiment of the invention, the average diameter of a bead is between about 1000 nm and about 1500 nm. In one embodiment of the invention, the average diameter of a bead is between about 1500 nm and about 2000 nm. In one embodiment of the invention, the average diameter of a bead is between about 2000 nm and about 2500 nm. In one embodiment of the invention, the average diameter of a bead is between about 2500 nm and about 3000 nm. In one embodiment of the invention, the average diameter of a bead is between about 3000 nm and about 3500 nm. In one embodiment of the invention, the average diameter of a bead is between about 3500 nm and about 4000 nm. In one embodiment of the invention, the average diameter of a bead is between about 4000 nm and about 4500 nm. In one embodiment of the invention, the average diameter of a bead is between about 4500 nm and about 5000 nm. In one embodiment of the invention, the average diameter of a bead is between about 5000 nm and about 5500 nm. In one embodiment of the invention, the average diameter of a bead is between about 5500 nm and about 6000 nm. In one embodiment of the invention, the average diameter of a bead is between about 6000 nm and about 6500 nm. In one embodiment of the invention, the average diameter of a bead is between about 6500 nm and about 7000 nm. In one embodiment of the invention, the average diameter of a bead is between about 7000 nm and about 7500 nm. In one embodiment of the invention, the average diameter of a bead is between about 7500 nm and about 8000 nm. In one embodiment of the invention, the average diameter of a bead is between about 8000 nm and about 8500 nm. In one embodiment of the invention, the average diameter of a bead is between about 8500 nm and about 9000 nm. In one embodiment of the invention, the average diameter of a bead is between about 9000 nm and about 9500 nm. In one embodiment of the invention, the average diameter of a bead is between about 9500 nm and about 10000 nm. In another embodiment the aforementioned fiber is bead-free. In certain embodiments, an additive (such a polyethyleneoxide) can be added to the electroprocessing process to control the number and size of the beads.

In one embodiment, said aforementioned electrospun fiber, along a plurality of said electrospun fibers, forms an electrospun fiber mat. In certain embodiments, the fibers within the mat are uniform. In certain embodiments, the mat is composed solely of fibers randomly oriented in a plane.

In certain embodiments of the invention, said electrospun fiber mat may exhibit pore sizes of between about 0.01 microns to about 100 microns. In certain embodiments, the mat may exhibit pore sizes of between about 0.1 microns to about 100 microns. In certain embodiments, the mat may exhibit pore sizes of between about 0.1 microns to about 50 microns. In certain embodiments, the mat may exhibit pore sizes of between about 0.1 microns to about 10 microns. In certain embodiments, the mat may exhibit pore sizes of between about 0.1 microns to about 5 microns. In certain embodiments, the mat may exhibit pore sizes of between about 0.1 microns to about 2 microns. In certain embodiments, the mat may exhibit pore sizes of between about 0.2 microns to about 1.5 microns. In certain embodiments, the pore size may be non-uniform. In certain embodiments, the pore size may be uniform.

In certain embodiments of the invention, said electrospun fiber mat has a surface area of between about 0.1 $m^2/g$ and about 1000 $m^2/g$. In certain embodiments of the invention, said electrospun fiber mat has a surface area of between about 1 $m^2/g$ and about 1000 $m^2/g$. In certain embodiments of the invention, said electrospun fiber mat has a surface area of between about 10 $m^2/g$ and about 1000 $m^2/g$.

In one embodiment of the invention, a parallel plate setup is used in the electrospinning In one embodiment, electrospinning is conducted with the aid of any suitable apparatus as will be known to one skilled in the art.

In one embodiment of the invention, the voltage applied in the electrospinning is from about 5 to about 50 KV. In certain embodiments, the voltage applied in the electrospinning is from about 10 to about 40 KV. In certain embodiments, the voltage applied in the electrospinning is from about 15 to about 35 KV. In certain embodiments, the voltage applied in the electrospinning is from about 20 to about 30 KV. In certain embodiments, the voltage applied in the electrospinning is about 29 KV.

In one embodiment of the invention, the distance between electrodes in the electrospinning is from about 10 to about 100 cm. In certain embodiments, the distance between electrodes in the electrospinning is from about 10 to about 75 cm. In certain embodiments, the distance between electrodes in the electrospinning is from about 20 to about 50 cm. In certain embodiments, the distance between electrodes in the electrospinning is about 30 cm.

In one embodiment of the invention, the flow rate in the electrospinning is from about 0.005 mL/min and about 0.5 mL/min. In certain embodiments, the flow rate in the electrospinning is from about 0.01 mL/min and 0.1 mL/min. In certain embodiments, the flow rate in the electrospinning is from 0.01 mL/min and 0.05 mL/min. In certain embodiments, the flow rate in the electrospinning is from 0.1 mL/min and 0.2 mL/min. In certain embodiments, the flow rate in the electrospinning is about 0.1 mL/min. All flow rates are given as per spinnerette.

In one embodiment of the invention, the electric current in the electrospinning is from about 10 nA and about 10,000 nA. In certain embodiments, the electric current in the electrospinning is from about 10 nA and about 1000 nA. In certain embodiments, the electric current in the electrospinning is from about 50 nA and about 500 nA. In certain embodiments, the electric current in the electrospinning is from about 75 nA and about 100 nA. In certain embodiments, the electric current in the electrospinning is around about 85 nA.

For the electroprocessing described herein, solvent can be used that allows delivery of the material or substance to the orifice, tip of a syringe, or other site from which the material will be electroprocessed. The solvent may be used for dissolving or suspending the material or the substance to be electroprocessed. Solvents useful for dissolving or suspending a material or a substance depend on the material or substance. Electrospinning techniques often require more specific solvent conditions. For example, certain monomers can be electrodeposited as a solution or suspension in water, 2,2,2-trifluoroethanol, 1,1,1,3,3,3-hexafluoro-2-propanol (also known as hexafluoroisopropanol or HFIP), isopropanol or other lower order alcohols, especially halogenated alcohols, may be used. Other solvents that may be used or combined with other solvents in electroprocessing natural matrix materials include acetamide, N-methylformamide, N,N-dimethylformamide (DMF), dimethylsulfoxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, and hexafluoroacetone.

Layer-by-Layer Deposition

In certain embodiments, the electrospun fibers are coated via a layer-by-layer (LbL) deposition process (see, for example, U.S. Pat. No. 7,220,452, hereby incorporated by reference). Exemplary layer-by-layer deposition techniques involve sequentially dipping a electrospun fiber into a pair of coating solutions. Alternatively, a electrospun fiber may be sprayed with a solution in a spray or mist form. One coating process embodiment involves solely dip-coating and optionally dip-rinsing steps. Another coating process embodiment involves solely spray-coating and optionally spray-rinsing steps. Of course, a number of alternatives involve various combinations of spray- and dip-coating and optionally spray- and dip-rinsing steps may be designed by a person having ordinary skill in the art.

For example, a solely dip-coating process involves the steps of immersing a electrospun fiber in a solution of a charged polymeric material; optionally rinsing the electrospun fiber by immersing the electrospun fiber in a rinsing solution; immersing said electrospun fiber in a solution of an oppositely charge polymeric material; and optionally rinsing said electrospun fiber in a rinsing solution, thereby forming a bilayer of the charged polymeric materials. This bilayer formation process may be repeated a plurality of times in order to produce a thicker layer-by-layer coating.

The immersion time for each of the coating and optional rinsing steps may vary depending on a number of factors. Preferably, immersion of the core material into a coating solution occurs over a period of about 1 to 30 minutes, more preferably about 1 to 20 minutes, and most preferably about 1 to 5 minutes. Rinsing may be accomplished with a plurality of rinsing steps, but a single rinsing step, if desired, can be quite efficient.

Another embodiment of the coating process involves a series of spray coating techniques. The process generally includes the steps of spraying a core material of a electrospun fiber with a solution of a charged polymeric material; optionally rinsing the electrospun fiber by spraying the electrospun fiber with a rinsing solution and then optionally drying the electrospun fiber; spraying the electrospun fiber with a solution of a non-charged polymeric material which can be non-covalently bond to the charged polymeric material on the electrospun fiber; optionally rinsing the electrospun fiber by spraying the electrospun fiber with a rinsing solution, thereby to form a bilayer of the charged polymeric material and the non-charged polymeric material. This bilayer formation procedure may be repeated a plurality of times in order to produce a thicker layer-by-layer coating.

The spray coating application may be accomplished via a process selected from the group consisting of an air-assisted atomization and dispensing process, an ultrasonic-assisted atomization and dispensing process, a piezoelectric assisted atomization and dispensing process, an electromechanical jet printing process, a piezo-electric jet printing process, a piezo-electric with hydrostatic pressure jet printing process, and a thermal jet printing process; and a computer system capable of controlling the positioning of the dispensing head of the spraying device on the ophthalmic lens and dispensing the coating liquid. By using such spraying coating processes, an asymmetrical coating can be applied to a electrospun fiber.

In accordance with the present invention, coating solutions can be prepared in a variety of ways. In particular, a coating solution of the present invention can be formed by dissolving a charged polymeric material in water or any other solvent capable of dissolving the materials. When a solvent is used, any solvent that can allow the components within the solution to remain stable in water is suitable. For example, an alcohol-based solvent can be used. Suitable alcohol can include, but are not limited to, isopropyl alcohol, hexanol, ethanol, etc. It should be understood that other solvents commonly used in the art can also be suitably used in the present invention.

Whether dissolved in water or in a solvent, the concentration of a material (i.e., a charged polymeric material) in a solution of the present invention can generally vary depending on the particular materials being utilized, the desired coating thickness, and a number of other factors.

It may be typical to formulate a relatively dilute aqueous solution of charged polymeric material. For example, a charged polymeric material concentration can be between about 0.0001% to about 0.25% by weight, between about 0.005% to about 0.10% by weight, or between about 0.01% to about 0.05% by weight.

In general, the charged polymeric solutions mentioned above can be prepared by any method well known in the art for preparing solutions. Once dissolved, the pH of the solution can also be adjusted by adding a basic or acidic material. For example, a suitable amount of 1 N hydrochloric acid (HCl) can be added to adjust the pH to about 2.5.

Where a solid polyelectrolyte comprises at least one bilayer of a first charged polymeric material and a second charged polymeric material having charges opposite of the charges of the first charged polymeric material, it may be desirable to apply a solution containing both the first and second charged polymeric materials within a single solution. For example, a polyanionic solution can be formed as described above, and then mixed with a polycationic solution that is also formed as described above. The solutions can then be mixed slowly to form a coating solution. The amount of each solution applied to the mix depends on the molar charge ratio desired. For example, if a 10:1 (polyanion:polycation) solution is desired, 1 part (by volume) of the polycation solution can be mixed into 10 parts of the polyanion solution. After mixing, the solution can also be filtered if desired.

One aspect of the invention relates to a method of forming a coating on an electrospun fiber, comprising the steps of:

(a) contacting the electrospun fiber with a solution of a first charged polymeric material to form a layer of the charged polymeric material;

(b) optionally rinsing the resulting electrospun fiber by contacting said surface with a rinsing solution;

(c) contacting said the optionally rinsed electrospun fiber with a solution of a second charged polymeric material, to form a layer of the second charged polymeric material on top of the layer of the first charged polymeric material, thereby forming a bilayer; and (d) optionally rinsing the resulting electrospun fiber by contacting said electrospun fiber with a rinsing solution;

wherein each bilayer comprises a polycationic layer and a polyanionic layer.

In certain embodiments, the present invention relates to any one of the aforementioned methods and/or membrane made thereby, wherein at least one of said contacting occurs by immersion the electrospun fiber in a solution.

In certain embodiments, the present invention relates to any one of the aforementioned methods and/or membrane made thereby, wherein at least one of said contacting occurs by immersion the electrospun fiber in a solution with a pH of between about 7 to about 11. In certain embodiments, the present invention relates to any one of the aforementioned methods and/or membrane made thereby, wherein at least one of said contacting occurs by immersion the electrospun fiber in a solution with a pH of between about 8 and about 10. In certain embodiments, the present invention relates to any one of the aforementioned methods and/or membrane made thereby, herein at least one of said contacting occurs by immersion the electrospun fiber in a solution with a pH of about 9.

In certain embodiments, the present invention relates to any one of the aforementioned methods and/or membrane made thereby, wherein the number of bilayers is about 5. In certain embodiments, the present invention relates to any one of the aforementioned methods and/or membrane made thereby, wherein the number of bilayers is about 10. In certain embodiments, the present invention relates to any one of the aforementioned methods and/or membrane made thereby, wherein the number of bilayers is about 20. In certain embodiments, the present invention relates to any one of the aforementioned methods and/or membrane made thereby, wherein the number of bilayers is about 30. In certain embodiments, the present invention relates to any one of the aforementioned methods and/or membrane made thereby, wherein the number of bilayers is about 40. In certain embodiments, the present invention relates to any one of the aforementioned methods and/or membrane made thereby, wherein the number of bilayers is about 50. In certain embodiments, the present invention relates to any one of the aforementioned methods and/or membrane made thereby, wherein the number of bilayers is about 75. In certain embodiments, the present invention relates to any one of the aforementioned methods and/or membrane made thereby, wherein the number of bilayers is about 100. In certain embodiments, the present invention relates to any one of the aforementioned methods and/or membrane made thereby, wherein the number of bilayers is about 125. In certain embodiments, the present invention relates to any one of the aforementioned methods and/or membrane made thereby, wherein the number of bilayers is about 150.

In certain embodiments, the present invention relates to any one of the aforementioned methods and/or membrane made thereby, wherein the number of bilayers is 1 to 5. In certain embodiments, the present invention relates to any one of the aforementioned methods and/or membrane made thereby, wherein the number of bilayers is 5 to 10. In certain embodiments, the present invention relates to any one of the aforementioned methods and/or membrane made thereby, wherein the number of bilayers is 10 to 15. In certain embodiments, the present invention relates to any one of the aforementioned methods and/or membrane made thereby, wherein the number of bilayers is 15 to 20. In certain embodiments, the present invention relates to any one of the aforementioned methods and/or membrane made thereby, wherein the number of bilayers is 20 to 25. In certain embodiments, the present invention relates to any one of the aforementioned methods and/or membrane made thereby, wherein the number of bilayers is 1 to 25. In certain embodiments, the present invention relates to any one of the aforementioned methods and/or membrane made thereby, wherein the number of bilayers is 25 to 30. In certain embodiments, the present invention relates to any one of the aforementioned methods and/or membrane made thereby, wherein the number of bilayers is 30 to 35. In certain embodiments, the present invention relates to any one of the aforementioned methods and/or membrane made thereby, wherein the number of bilayers is 35 to 40. In certain embodiments, the present invention relates to any one of the aforementioned methods and/or membrane made thereby, wherein the number of bilayers is 40 to 45. In certain embodiments, the present invention relates to any one of the aforementioned methods and/or membrane made thereby, wherein the number of bilayers is 45 to 50.

In certain embodiments, the present invention relates to any one of the aforementioned methods and/or membrane made thereby, wherein the number of bilayers is about 25 to about 50. In certain embodiments, the present invention relates to any one of the aforementioned methods and/or membrane made thereby, wherein the number of bilayers is about 50 to about 75. In certain embodiments, the present invention relates to any one of the aforementioned methods and/or membrane made thereby, wherein the number of bilayers is about 75 to about 100. In certain embodiments, the present invention relates to any one of the aforementioned methods and/or membrane made thereby, wherein the number of bilayers is about 100 to about 150. In certain embodiments, the present invention relates to any one of the aforementioned methods and/or membrane made thereby, wherein the number of bilayers is about 150 to about 200. In certain embodiments, the present invention relates to any one of the aforementioned methods and/or membrane made thereby, wherein the number of bilayers is 1 to about 1000.

In certain embodiments, the present invention relates to any one of the aforementioned methods and/or membrane made thereby, wherein the number of bilayers is x.5, wherein x is an integer (i.e., there is an "extra" cationic or anionic layer).

In certain embodiments, the present invention relates to the aforementioned method, wherein said polycationic layers and polyanionic layers form a polymer coating which is of a uniform thickness (i.e., said thickness does not vary more than about 10% over the surface; or by more than about 5% over the surface; or by more than about 1% over the surface). In certain embodiments, said polycationic layers and polyanionic layers form a polymer coating which has a mass per surface area of less than about 500 μg/$cm^2$. In certain embodiments, said polycationic layers and polyanionic layers form a polymer coating which has a mass per surface area of less than about 100 μg/$cm^2$. In certain embodiments, said polycationic layers and polyanionic layers form a polymer coating which has a mass per surface area of less than about 50 μg/$cm^2$. In certain embodiments, said polycationic layers and polyanionic layers form a polymer coating which has a mass per surface area of less than about 10 μg/$cm^2$. In certain embodiments, said polycationic layers and polyanionic layers form a polymer coating which has a mass per surface area of less than about 5 μg/$cm^2$.

In certain embodiments, said polycationic layers and polyanionic layers form a polymer coating which has an average thickness of about 70 nm. In certain embodiments, said polycationic layers and polyanionic layers form a polymer coating which has an average thickness of about 80 nm. In certain embodiments, said polycationic layers and polyanionic layers form a polymer coating which has an average thickness of about 90 nm. In certain embodiments, said polycationic layers and polyanionic layers form a polymer coating which has an average thickness of about 100 nm.

Polycations

In certain embodiments, the polycations of the invention are defined as polymeric molecules having a multiplicity (i.e., more than three) of cationic charges per polymeric molecule, or a net cationic charge excess of greater than three charges per polymeric molecule. In certain embodiments, the polycations are hydrocarbon polymers, with significant hydrophobic character, which contain a multiplicity of nitrogen-containing moieties with a pKa of greater than or equal to about 8. This means that, at conditions below a pH of 8, a significant portion of the nitrogen-containing moieties (e.g., amino, guandinyl or biguandinyl groups) will be protonated and cationic.

In certain embodiments, the polycations of the invention are polymers having an average degree of polymerization of between about 3 and about 25,000. In certain embodiments, the polycations of the invention are polymers having an average degree of polymerization of between about 20 and about 10,000. In certain embodiments, the polycations of the invention are polymers having an average degree of polymerization of between about 100 and about 2,500.

In certain embodiments, the polycation is a polymer comprising a plurality of guanidines, quaternary ammoniums, biguanides, or salts thereof.

In certain embodiments, the polycation is a polymer comprising a plurality of subunits selected from the group consisting of

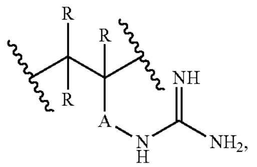

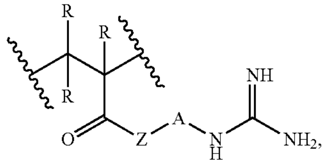

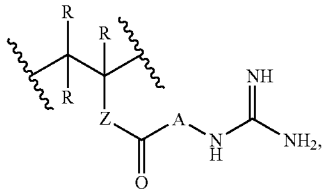

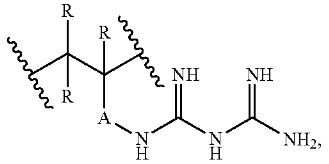

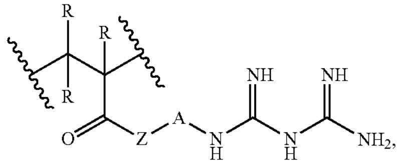

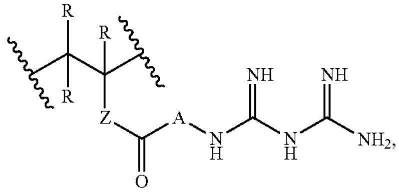

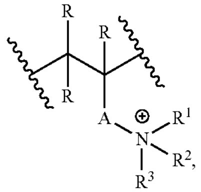

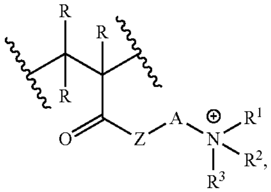

-continued

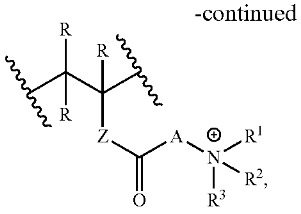

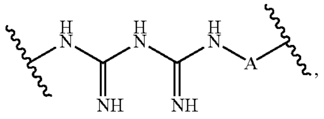

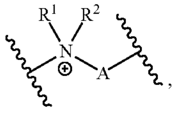

and salts thereof;

wherein, independently for each occurrence,

Z is absent, —O—, —S—, or —N(R)—;

A is absent or selected from the group consisting of alkylene, arylene, heteroarylene, alkylene-arylene, alkylene-heteroarylene, arylene-alkylene, heteroarylene-alkylene, alkylene-arylene-alkylene, and alkylene-heteroarylene-alkylene;

R is hydrogen or alkyl;

$R^1$ is hydrogen or alkyl;

$R^2$ is alkyl; and $R^3$ is alkyl.

In certain embodiments, the invention relates to any one of the aforementioned polycations, wherein the polycation comprises a plurality of subunits selected from the group consisting of

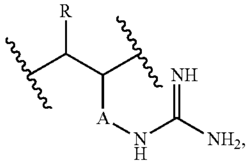

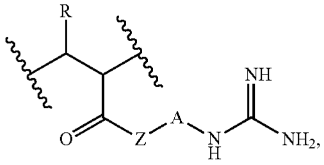

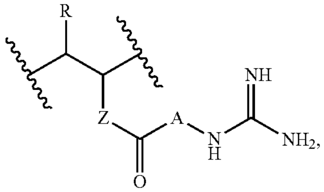

and salts thereof.

In certain embodiments, the invention relates to any one of the aforementioned polycations, wherein the polycation comprises a plurality of subunits selected from the group consisting of

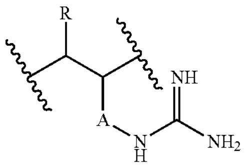

and salts thereof.

In certain embodiments, the invention relates to any one of the aforementioned polycations, wherein the polycation comprises a plurality of subunits selected from the group consisting of

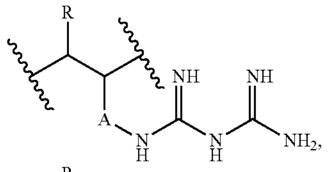

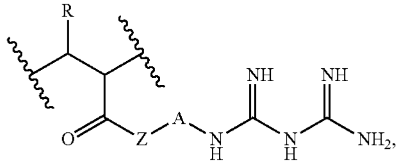

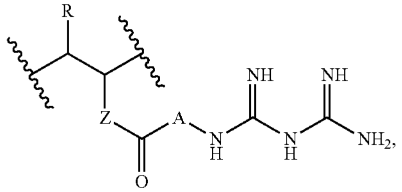

and salts thereof.

In certain embodiments, the invention relates to any one of the aforementioned polycations, wherein the polycation comprises a plurality of subunits selected from the group consisting of

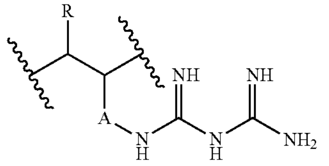

and salts thereof.

In certain embodiments, the invention relates to any one of the aforementioned polycations, wherein the polycation comprises a plurality of subunits selected from the group consisting of

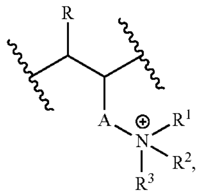

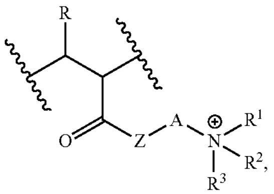

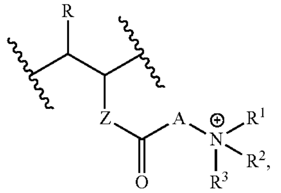

and salts thereof.

In certain embodiments, the invention relates to any one of the aforementioned polycations, wherein the polycation comprises a plurality of subunits selected from the group consisting of

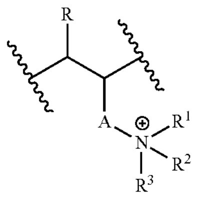

and salts thereof.

In certain embodiments, the invention relates to any one of the aforementioned polycations, wherein the polycation comprises a plurality of subunits selected from the group consisting of

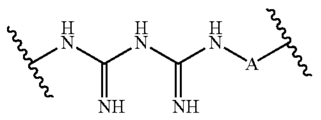

and salts thereof.

In certain embodiments, the invention relates to any one of the aforementioned polycations, wherein the polycation comprises a plurality of subunits selected from the group consisting of

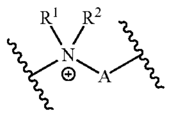

and salts thereof.

In certain embodiments, the invention relates to any one of the aforementioned polycations, wherein Z is absent.

In certain embodiments, the invention relates to any one of the aforementioned polycations, wherein Z is —N(R)—.

In certain embodiments, the invention relates to any one of the aforementioned polycations, wherein Z is —N(H)—.

In certain embodiments, the invention relates to any one of the aforementioned polycations, wherein A is absent.

In certain embodiments, the invention relates to any one of the aforementioned polycations, wherein A is alkylene.

In certain embodiments, the invention relates to any one of the aforementioned polycations, wherein A is hexamethylene.

In certain embodiments, the invention relates to any one of the aforementioned polycations, wherein A is arylene.

In certain embodiments, the invention relates to any one of the aforementioned polycations, wherein A is phenylene.

In certain embodiments, the invention relates to any one of the aforementioned polycations, wherein R is hydrogen.

In certain embodiments, the invention relates to any one of the aforementioned polycations, wherein R is alkyl.

In certain embodiments, the invention relates to any one of the aforementioned polycations, wherein R is methyl.

In certain embodiments, the invention relates to any one of the aforementioned polycations, wherein $R^1$ is hydrogen.

In certain embodiments, the invention relates to any one of the aforementioned polycations, wherein $R^1$ is alkyl.

In certain embodiments, the invention relates to any one of the aforementioned polycations, wherein $R^1$ is methyl.

In certain embodiments, the invention relates to any one of the aforementioned polycations, wherein $R^2$ is methyl.

In certain embodiments, the invention relates to any one of the aforementioned polycations, wherein $R^3$ is methyl.

In certain embodiments, the invention relates to any one of the aforementioned polycations, wherein said salt is a halide.

In certain embodiments, the invention relates to any one of the aforementioned polycations, wherein said salt is a chloride.

In certain embodiments, the polycation is selected from the group consisting of poly(N-vinylguanidine) (PVG), poly(diallyl dimethyl ammonium chloride) (PDAC), polyarginine, polyallylaminehydrochloride (PAH), linear polyethyleneimine (LPEI), branched polyethyleneimine (BPEI), poly(amidoamine) dendrimer (PAMAM), poly(N-(1,3-bis(2-ethylhexyl)-5-methylhexahydropyrimidin-5-yl)acrylamide), poly (hexamethylenebiguanide) (PHMB), or poly (hexamethylene-5-(phenylene)biguanide.

In certain embodiments, the polycation is a poly(N-vinylguanidine) (PVG).

Polyanions

In certain embodiments, the polyanions of the invention are defined as polymeric molecules having a multiplicity (i.e., more than three) of anionic charges per polymeric molecule, or a net anionic charge excess of greater than three charges per polymeric molecule.

In certain embodiments, the polyanions of the invention are polymers having an average degree of polymerization of between about 3 and about 25,000. In certain embodiments, said polyanions are polymers having an average degree of polymerization of between about 20 and about 10,000. In certain embodiments, said polyanions are polymers having an average degree of polymerization of between about 100 and about 2,500.

In certain embodiments, the polyanion is a polymer comprising hydroxamic acids, acrylamidoximes, or salts thereof.

In certain embodiments, the polyanion is a polymer comprising a plurality of subunits selected from the group consisting of

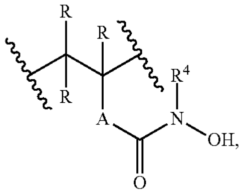

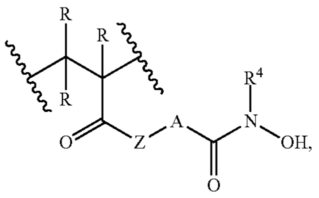

-continued

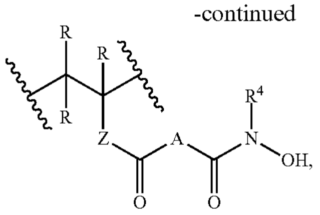

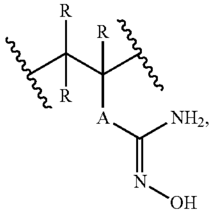

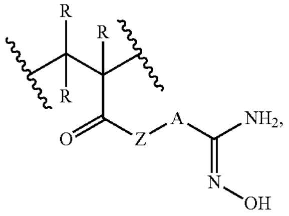

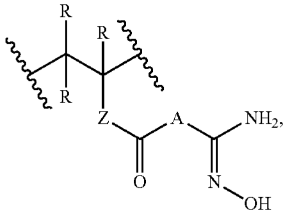

and salts thereof;

wherein, independently for each occurrence,

Z is —O—, —S—, or —N(R)—;

A is absent or selected from the group consisting of alkylene, arylene, heteroarylene, alkylene-arylene, alkylene-heteroarylene, arylene-alkylene, heteroarylene-alkylene, alkylene-arylene-alkylene, and alkylene-heteroarylene-alkylene;

R is hydrogen or alkyl; and $R^4$ is hydrogen or alkyl.

In certain embodiments, the invention relates to any one of the aforementioned polyanions, wherein the polyanion comprises a plurality of subunits selected from the group consisting of

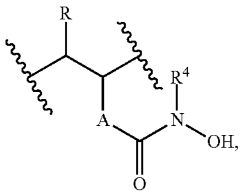

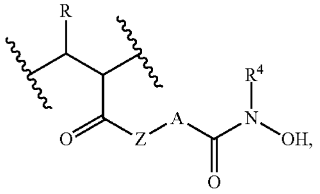

-continued

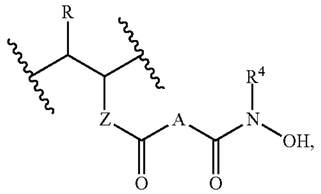

and salts thereof.

In certain embodiments, the invention relates to any one of the aforementioned polyanions, wherein the polyanion comprises a plurality of subunits selected from the group consisting of

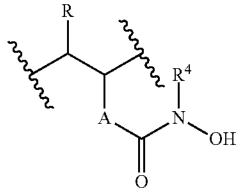

and salts thereof.

In certain embodiments, the invention relates to any one of the aforementioned polyanions, wherein the polyanion comprises a plurality of subunits selected from the group consisting of

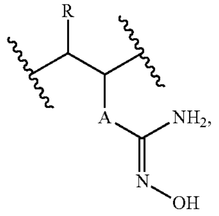

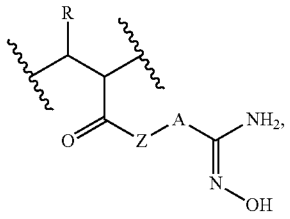

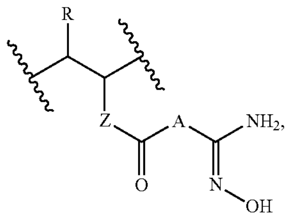

and salts thereof.

In certain embodiments, the invention relates to any one of the aforementioned polyanions, wherein the polyanion comprises a plurality of subunits selected from the group consisting of

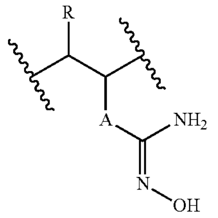

and salts thereof.

In certain embodiments, the invention relates to any one of the aforementioned polycations, wherein Z is absent.

In certain embodiments, the invention relates to any one of the aforementioned polycations, wherein Z is —N(R)—.

In certain embodiments, the invention relates to any one of the aforementioned polycations, wherein Z is —N(H)—.

In certain embodiments, the invention relates to any one of the aforementioned polycations, wherein R is hydrogen.

In certain embodiments, the invention relates to any one of the aforementioned polycations, wherein R is methyl.

In certain embodiments, the invention relates to any one of the aforementioned polycations, wherein $R^4$ is hydrogen.

In certain embodiments, the invention relates to any one of the aforementioned polycations, wherein $R^4$ is methyl.

In certain embodiments, the invention relates to any one of the aforementioned polycations, wherein A is absent.

In certain embodiments, the invention relates to any one of the aforementioned polycations, wherein A is alkylene.

In certain embodiments, the invention relates to any one of the aforementioned polycations, wherein A is arylene.

Figure 15:
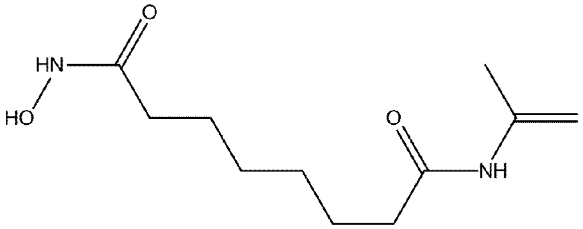
FIG. 15 depicts selected hydroxamic acid-containing monomers.
Figure 15:
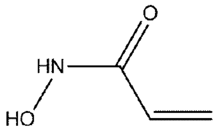
Figure 15:
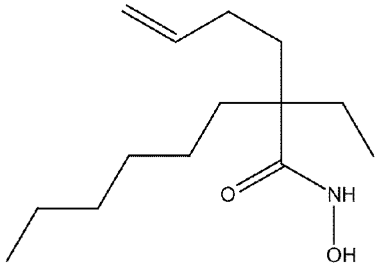
Figure 15:
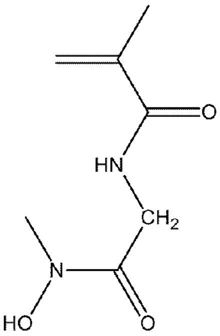

In certain embodiments, the polyanion is poly(N-hydroxyacrylamide) (PHA), poly(N-hydroxyacrylamidoxamate), poly(octanedioic acid hydroxyamide ispropenylamide), poly (2-ethyl-2-hexyl-hex-5-enoic acid hydroxyamide), poly(N-[(hydroxy-methyl-carbamoyl)-methyl]-2-methyl-acrylamide, or a salt thereof. Selected hydroxamic acid-containing monomers are shown in FIG. 15.

Selected Properties of the Coated Electrospun Nanofibers

An advantage of the LbL electrostatic assembly discussed above is that, by selecting appropriate polyelectrolytes of opposite charges and varying functionalities, one can generate multifunctional electrospun, fiber-based protection fabrics for both chemical and biological protection. In certain embodiments, multifunctionality is generated by using the layer-by-layer deposition method with two functional polyelectrolytes, a polycation and a polyanion, which are antimicrobial and esterolytic, respectively. In certain embodiments, more than one polycation or polyanion, each with a different functionality, may be envisioned, so that two or more functionalities can be realized on a single fabric. In other embodiments, other methods of conformal deposition, such as chemical vapor deposition and dip-coating, may be used to generate multifunctionality.

Antimicrobial Properties.

In certain embodiments, the membranes of the invention have antimicrobial properties due to the polycationic portion of the polymer coating. In certain embodiments, the polycations of the invention target Gram-negative and/or Gram-positive bacteria. The term 'Gram-positive bacteria' is an art recognized term for bacteria characterized by having as part of their cell wall structure peptidoglycan as well as polysaccharides and/or teichoic acids and are characterized by their blue-violet color reaction in the Gram-staining procedure. Representative Gram-positive bacteria include: *actinomyces* spp., *Bacillus anthracis, Bifidobacterium* spp., *Clostridium botulinum, Clostridium perfringens, Clostridium* spp., *Clostridium tetani, Corynebacterium diphtheriae, Corynebacterium jeikeium, Enterococcus faecalis, Enterococcus faecium, Erysipelothrix rhusiopathiae, Eubacterium* spp., *Gardnerella vaginalis, Gemella morbillorum, Leuconostoc* spp., *Mycobacterium abcessus, Mycobacterium avium* complex, *Mycobacterium chelonae, Mycobacterium fortuitum, Mycobacterium haemophilium, Mycobacterium kansasii, Mycobacterium leprae, Mycobacterium marinum, Mycobacterium scrofulaceum, Mycobacterium smegmatis, Mycobacterium terse, Mycobacterium tuberculosis, Mycobacterium ulcerans, Nocardia* spp., *Peptococcus niger, Peptostreptococcus* spp., *Proprionibacterium* spp., *Staphylococcus aureus, Staphylococcus auricularis, Staphylococcus capitis, Staphylococcus cohnii, Staphylococcus epidermidis, Staphylococcus haemolyticus, Staphylococcus hominis, Staphylococcus lugdanensis, Staphylococcus saccharolyticus, Staphylococcus saprophyticus, Staphylococcus schleiferi, Staphylococcus similans, Staphylococcus warneri, Staphylococcus xylosus, Streptococcus agalactiae* (group B *streptococcus*), *Streptococcus anginosus, Streptococcus bovis, Streptococcus canis, Streptococcus equi, Streptococcus milleri, Streptococcus mitior, Streptococcus mutans, Streptococcus pneumoniae, Streptococcus pyogenes* (group A *streptococcus*), *Streptococcus salivarius, Streptococcus sanguis*. The term "Gram-negative bacteria" is an art recognized term for bacteria characterized by the presence of a double membrane surrounding each bacterial cell. Representative Gram-negative bacteria include *Acinetobacter calcoaceticus, Actinobacillus actinomycetemcomitans, Aeromonas hydrophile, Alcaligenes xylosoxidans, Bacteroides, Bacteroides fragilis, Bartonella bacilliformis, Bordetella* spp., *Borrelia burgdorferi, Branhamella catarrhalis, Brucella* spp., *Campylobacter* spp., *Chalmydia pneumoniae, Chlamydia psittaci, Chlamydia trachomatis, Chromobacterium violaceum, Citrobacter* spp., *Eikenella corrodens, Enterobacter aerogenes, Escherichia coli, Flavobacterium meningosepticum, Fusobacterium* spp., *Haemophilus influenzae, Haemophilus* spp., *Helicobacter pylori, Klebsiella* spp., *Legionella* spp., *Leptospira* spp., *Moraxella catarrhalis, Morganella morganii, Mycoplasma pneumoniae, Neisseria gonorrhoeae, Neisseria meningitidis, Pasteurella multocida, Plesiomonas shigelloides, Prevotella* spp., *Proteus* spp., *Providencia rettgeri, Pseudomonas aeruginosa, Pseudomonas* spp., *Rickettsia prowazekii, Rickettsia rickettsii, Rochalimaea* spp., *Salmonella* spp., *Salmonella typhi, Serratia marcescens, Shigella* spp., *Treponema carateum, Treponema pallidum, Treponema pallidum endemicum, Treponema pertenue, Veillonella* spp., *Vibrio cholerae, Vibrio vulnificus, Yersinia enterocolitica, Yersinia pestis.*

Esterolytic Properties.

In certain embodiments, the membranes of the invention have esterolytic properties due to the polyanionic portion of the polymer coating. Exemplary phosphate esters which can be hydrolyzed are phosphates, phosphorofluoridates, phosphonates, and their sulfur analogs such as phosphorothionates. Exemplary organophosphate esters include parathion, malathion, diazinon, phosmet (Imidan®), chlorpyrifos (Lorsban®), sarin, tabun (ethylphosphorodimethyl-amidocyanidate), soman (pinacolyl methylphospphonerfluoridate), GF (Cyclohexyl methylphosphonofluoridate) and VX (ethyl S-2-diisopropyl aminoethyl methylphosphoro-thioate).

Breathability.

In certain embodiments, the membranes of the invention exhibit high breathability. In certain embodiments, the membranes of the invention exhibit high breathability while still maintaining wind resistance. In certain embodiments, the breathability is afforded by the porosity of the electrospun nanofibers that is preserved when nanofibers are functionalized by chemical or physical bonding of the polyelectrolyte multilayer.

In certain embodiments, the air flow resistance of the membrane is about $10^7$ $m^{-1}$ to about $10^{13}$ $m^{-1}$. In certain embodiments, the air flow resistance of the membrane is about $10^7$ $m^{-1}$ to about $10^8$ $m^{-1}$. In certain embodiments, the air flow resistance of the membrane is about $10^8$ $m^{-1}$ to about $10^9$ $m^{-1}$. In certain embodiments, the air flow resistance of the membrane is about $10^9$ $m^{-1}$ to about $10^{10}$ $m^{-1}$. In certain embodiments, the air flow resistance of the membrane is about $10^{10}$ $m^{-1}$ to about $10^{11}$ $m^{-1}$. In certain embodiments, the air flow resistance of the membrane is about $10^{11}$ $m^{-1}$ to about $10^{12}$ $m^{-1}$. In certain embodiments, the air flow resistance of the membrane is about $10^{12}$ $m^{-1}$ to about $10^{13}$ $m^{-1}$.

In certain embodiments, the airflow resistivity of the membrane is about $1\times10^{14}$ $l/m^2$ to about $1\times10^{12}$ $l/m^2$. In certain embodiments, the airflow resistivity of the membrane is about $0.7\times10^{13}$ $l/m^2$ to about $1.7\times10^{13}$ $l/m^2$. In certain embodiments, the airflow resistivity of the membrane is about $1.0\times10^{13}$ $l/m^2$ to about $1.4\times10^{13}$ $l/m^2$.

In certain embodiments, the water vapor diffusion resistance of the membrane is about 50 s/m to about 350 s/m at a relative humidity of between about 0.3 and 0.7. In certain embodiments, the water vapor diffusion resistance of the membrane is about 100 s/m to about 300 s/m at a relative humidity of between about 0.3 and 0.7. In certain embodiments, the water vapor diffusion resistance of the membrane is about 100 s/m to about 150 s/m at a relative humidity of between about 0.3 and 0.7. In certain embodiments, the water vapor diffusion resistance of the membrane is about 100 s/m to about 150 s/m at a relative humidity of between about 0.3 and 0.7. In certain embodiments, the water vapor diffusion resistance of the membrane is about 150 s/m to about 200 s/m at a relative humidity of between about 0.3 and 0.7. In certain embodiments, the water vapor diffusion resistance of the membrane is about 200 s/m to about 250 s/m at a relative humidity of between about 0.3 and 0.7. In certain embodiments, the water vapor diffusion resistance of the membrane is about 250 s/m to about 300 s/m at a relative humidity of between about 0.3 and 0.7.

In certain embodiments, the water vapor diffusion resistivity of the membrane is about $1\times10^5$ $s/m^2$ to about $1\times10^7$ $s/m^2$ at a relative humidity of between about 0.3 and 0.7. In certain embodiments, the water vapor diffusion resistivity of the membrane is about $1\times10^6$ $s/m^2$ to about $2\times10^6$ $s/m^2$ at a relative humidity of between about 0.3 and 0.7.

Selected Applications

In certain embodiments, the invention relates to the production of multifunctional fabrics and articles made therefrom, which fabrics and articles do not lose the desirable attributes of comfort, soft hand, absorbency, better appearance which have heretofore been available only by utilization of naturally occurring articles. In other embodiments, the coated electrospun nanofibers of the invention, and materials made therefrom, can be incorporated into a textile or other apparel starting material in the form of a layer (e.g., a liner layer). The obtained raw wearing apparel material may then be used to make a protective garment, glove, sock, footwear (e.g., shoe), helmet, face mask and the like; the obtained wearing apparel may be worn in hazardous environments to protect the wearer from contact with viable microorganisms and/or organophosphorous esters.

The coated electrospun nanofibers of the invention, and materials made therefrom, can also be used on foods and plant species to reduce surface microbial populations and/or organophosphorous esters; used at manufacturing or processing sites handling such foods and plant species; or used to treat process waters around such sites. For example, the compositions can be used on food transport lines, food storage facilities; anti-spoilage air circulation systems; refrigeration and cooler equipment; beverage chillers and warmers, blanchers, cutting boards, third sink areas, and meat chillers or scalding devices.

The coated electrospun nanofibers of the invention, and materials made therefrom, can also be used to reduce microbial and viral counts, and/or organophosphorous esters, in air and liquids by incorporation into filtering media or breathing filters.

Other cleaning applications of the invention include clean-in-place (CIP) systems, clean-out-of-place (COP) systems, washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like.

Exemplification

The invention now being generally described, it will be more readily understood by reference to the following, which is included merely for purposes of illustration of certain aspects and embodiments of the present invention, and is not intended to limit the invention.

Methods for obtaining breathable, chemical and biological detoxifying protective fabrics, via functionalization of electrospun fiber mats using a layer-by-layer electrostatic assembly technique, are described below. Specifically, chemically reactive polyanion, poly(hydroxamic acid) (PHA), and bactericidal polycation, poly(N-vinylguanidine) (PVG), were synthesized and electrostatically assembled to generate multifunctional coatings on prefabricated polyacrylonitrile (PAN) fiber mats. In addition, the reactivity of PHA in the hydrolysis of diisopropyl fluorophosphate (DFP), a close analog of the chemical warfare agent sarin, was demonstrated. The DFP degradation rate with PHA was found to be comparable to that with compounds such as isonicotinhydroxamic acid methiodide, an efficient catalyst of organophosphate ester hydrolysis. It is also disclosed that protective fabrics functionalized with PVG/PHA layers were are able to degrade DFP mists, with DFP hydrolysis rates 60-fold higher than those with unmodified fabrics under identical conditions. Further, it was demonstrated that fabrics modified with PVG/PHA layers are bactericidal against *E. coli* and *S. epidermidis*. Breathability and barrier performance of functionalized fiber mats as protective fabrics were evaluated versus standard reference fabrics.

Materials

Polyacrylonitrile (PAN) ($M_w$ 150 kDa) was purchased from Scientific Polymer Products Inc. (Ontario, N.Y.) and used as received. Poly(acrylamide-co-acrylic acid) ($M_w$ 200 kDa, acrylamide 20 wt %), diisopropyl fluorophosphate (99%, DFP), hydroxylamine hydrochloride (99%), cyanamide (50 wt % in water) and N,N-dimethylformamide (DMF) were all obtained from Sigma-Aldrich Chemical Co. (St. Louis, Mo.) and used as received. Lupamin® 9095 (20-22% aqueous solution of polyvinylamine, average molecular weight 340 kDa) was kindly supplied by BTC (a specialty chemical distribution group of BASF, Germany). The porous expanded polytetrafluoroethylene (ePTFE) membrane was obtained from GE Energy (Lee's Summit, Mo.). The ePTFE membrane is supplied with a conformal oleophobic coating applied with a supercritical carbon dioxide process. The ePTFE membrane is approximately 0.02 mm thick, with an areal density of 0.0023 g/$m^2$ and porosity of about 50%. Bacteria *E. coli* (ATCC #67876) and *S. epidermidis* (ATCC #35984) were purchased from ATCC (Manassas, Va.) and stored at −80° C. prior to use.

Electrospinning

PAN solutions in DMF (10 wt %) were prepared by dissolving the polymer at 50-70° C. followed by stirring at room temperature. The PAN solutions were electrospun into fiber mats using a home-built parallel plate apparatus [Shin, Y. M.; Hohman, M. M.; Brenner, M. P.; Rutledge, G. C. *Polymer* 2001, 42, 9955]. The applied voltage (28-30 kV), the flow rate (0.015 mL/min) and the distance between the upper electrode and grounded collector (about 30 cm) were adjusted to stabilize the polymer jet to obtain fiber mats on the grounded collector.

Polymer Synthesis

Synthesis of poly(N-hydroxyacrylamide) (PHA).

Scheme 1 shows the modification of poly(acrylamide-co-acrylic acid) to poly(N-hydroxyacrylamide) (PHA) by reacting with hydroxylamine.

Scheme 1. Synthesis of poly(N-hydroxyacrylamide)

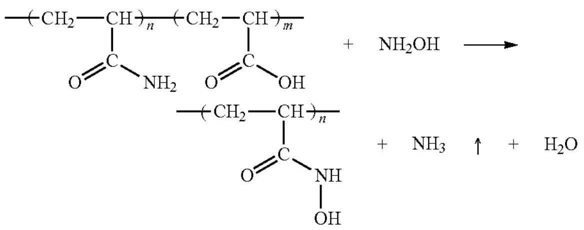

Poly(acrylamide-co-acrylic acid) was mixed with excess hydroxylamine hydrochloride in deionized water. The resulting solution was stirred for one day at 70° C. and then an aqueous solution of sodium hydroxide was added followed by stirring for three days at room temperature to convert completely into PHA solution. Conversion of poly(acrylic acid) and polyacrylamide into PHA by hydroxylamine is well-documented [Bromberg, L.; Schreuder-Gibson, H.; Creasy, W. R.; McGarvey, D. J.; Fry, R. A.; Hatton, T. A. *Ind. Eng. Chem. Res.* 2009, 48, 1650; Zhang, J.-F.; Hu, Y.-H.; Wang, D.-Z. *J. Cent. South Univ. Technol.* 2002, 9, 177; and Domb, A. J.; Cravalho, E. G.; Langer, R. J. *Polym. Sci., Pt A: Polym. Chem.* 1988, 26, 2623]. Release of ammonia by bubbling was observed. The solution was then frozen at −80° C. and lyophilized. The resultant PHA was dissolved in deionized water, dialyzed against excess deionized water and lyophilized. FTIR (KBr, $cm^{-1}$): 3600 (broad, —NHOH), 3430 (broad, OH stretching), 3210 (amide NH stretching), 1630 (CO—NH bending), 1450 ($CH_2$ scissor bending), 1425 (C—N stretching).

Synthesis of poly(N-vinylguanidine) (PVG).

Polyvinylamine (90% hydrolyzed) received as Lupamin 9095 was completely hydrolyzed by 37% hydrochloric acid at 80° C. followed by polymer purification by precipitation into 2M NaOH and dialysis (molecular weight cutoff, 12-14 kDa) and drying. Then polyvinylamine was completely guanidinylated by cyanamide following the previously described procedure [Bromberg, L.; Hatton, T. A. *Polymer* 2007, 48, 7490]. Scheme 2 shows the conversion of polyvinylamine to poly(N-vinylguanidine) by Guanidinylation.

Scheme 2. Synthesis of poly(N-vinylguanidine)

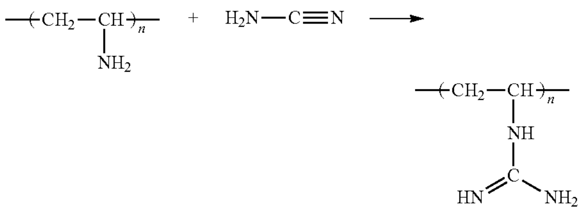

FTIR (KBr): 957 $cm^{-1}$ (C—N stretching), 1510 $cm^{-1}$ (C—N stretching), 1610 $cm^{-1}$ (NH, $NH_2$ deformation), 1670 $cm^{-1}$ (C═N stretching), 2940 $cm^{-1}$ (aliphatic $CH_2$ stretching). $^{13}C$ NMR ($D_2O$, ppm): 151.6 (C in the guanidinium group), 45.0 (methylene C in backbone), 35.5 (methane C in backbone).

Layer-by-Layer (LbL) Assembly Coating

LbL electrostatic assembly involves alternate adsorption of oppositely charged materials to construct the ultrathin coatings. PHA is a weak polyelectrolyte with $pK_a$ of 7.5, producing a negatively charged species at pH 9.0. Antimicrobial PVG is a strong polycation. The protonated PVG possesses a $pK_a$ of 13.4 and is positively charged over a broad range of pH [Bromberg, L.; Hatton, T. A. *Polymer* 2007, 48, 7490]. Aqueous solutions of PHA and PVG (10 mM, pH 9) were prepared and used for LbL assembly.

Electrospun fiber mats enable the generation of porous fabric scaffolds with tunable, high specific surface area (1-100 $m^2$/g) and surface properties. A broad range of electrospun polymer fiber mats have been demonstrated to be effective substrates for LbL-assembled, titanium dioxide-based functional coatings for protection against toxic industrial chemicals or mustard agents [Lee, J. A.; Krogman, K. C.; Ma, M.; Hill, R. M.; Hammond, P. T.; Rutledge, G. C. *Adv. Mater.* 2009, 21, 1252; and Krogman, K. C.; Lowery, J. L.; Zacharia, N. S.; Rutledge, G. C.; Hammond, P. T. *Nat. Mater.* 2009, 8, 512]. Use of the commercially available polymer, PAN, as a support matrix of electrospun fiber mats, is described below. Electrospun PAN fiber mats were plasma treated for 1 min (Harrick PDC-32G, Harrick Plasma Inc.) prior to LbL deposition. A Carl Zeiss DS50 programmable slide stainer was used for LbL deposition. Multilayer polyelectrolyte coatings on PAN fibers were produced by alternately dipping the fiber mat in 10 mM PVG and PHA aqueous solutions at room temperature [Gerenser, L. J. *J. Adhes. Sci. Technol.* 1993, 7, 1019; and Dupont-Gillain, C. C.; Adriaensen, Y.; Derclaye, S.; Rouxhet, P. G. *Langmuir* 2000, 16, 8194]. The dipping time in each polyelectrolyte solution was 60 min, followed by rinse in deionized water for 3 min.

Fiber Characterization

The fiber morphology was visualized by scanning electron microscopy (SEM, JEOL-6060). FTIR spectra were measured using a Nicolet 8700 spectrometer (Thermo Scientific Corp.) in the absorbance mode by accumulation of 256 scans with a resolution of 4 $cm^{-1}$. A Krato Axis Ultra Imaging XPS spectrometer (Kratos Analytical Co.) equipped with a monochromatized Al Kα X-ray source was used to analyze the surface chemistry of LbL-coated fibers. The take-off angle relative to the sample substrate was set at 20°. $^{13}C$ NMR spectra were carried out using a Bruker Avance 400 spectrometer operating at 100.61 MHz for $^{13}C$ at room temperature. Proton decoupling was applied and 15000 to 20000 scans were collected.

Figure 4:
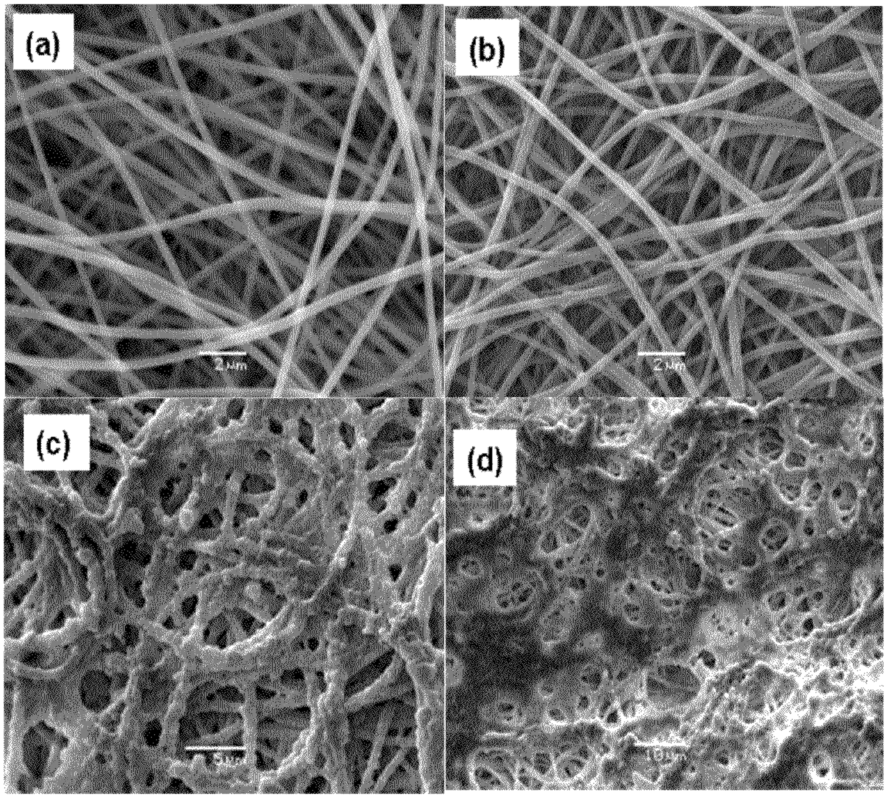
FIG. 4 depicts SEM images of (a) prefabricated PAN fiber mat (scale bar: 2 μm); (b) functionalized PAN fiber mat $(PVG/PHA)_{10}$ (scale bar: 2 μm); (c) functionalized PAN fiber mat $(PVG/PHA)_{20}$ (scale bar: 5 μm); and (d) functionalized PAN fiber mat $(PVG/PHA)_{30}$ (scale bar: 10 μm).

FIG. 4(*a*) shows a typical SEM image of PAN fiber mats electrospun from 10 wt % solution of DMF. The average diameter of the PAN fibers is about 350 nm with the fiber size ranging from 250 to 500 nm. The measured BET surface area of PAN fiber mats is about 15 $m^2/g$. FIG. 4(*b*) shows the typical fiber morphology of the functionalized PAN fiber mats with ten bilayers of PVG/PHA, denoted as $(PVG/PHA)_{10}$. Conformal coatings on individual fibers were observed over the fiber mat. The characteristic peak observed at 529 eV (O 1s) in the XPS spectra (not shown) shows the presence of oxygen on the surfaces of PAN fibers, which indicates the presence of PHA on the surfaces of functionalized fibers. With twenty bilayers of PVG/PHA coating, denoted as $(PHA/PVG)_{20}$, rough surface of functional coatings is clearly observed and the functional coatings start to bridge the pore structures in the fiber mats (FIG. 4(*c*)). As shown in FIG. 4(*d*), with 30 bilayers of the functional coating, $(PVG/PHA)_{30}$, surface pores are partially filled, which accounts for approximately 20-30% of pores. The observed closure of surface pores may affect the breathability of the fiber mats; this is discussed in more detail below.

Breathability Test

Figure 5A:
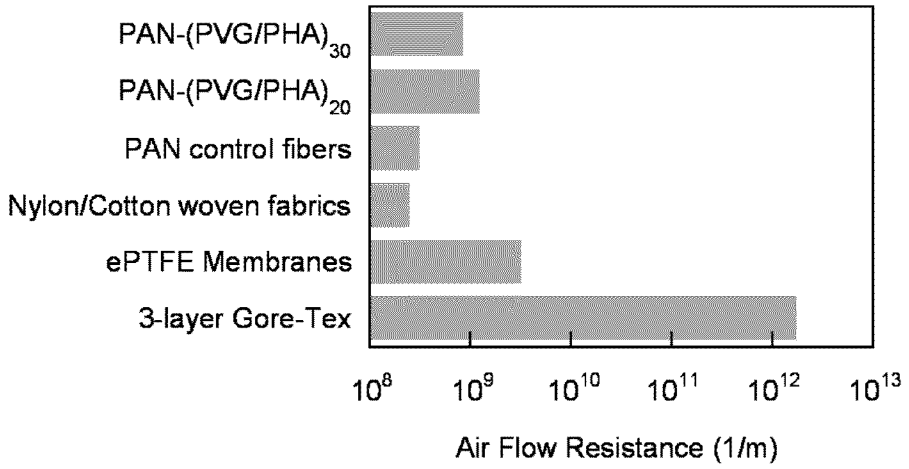
FIG. 5A depicts a bar graph comparing airflow resistance of functionalized fiber mats at a temperature of about 30° C. and at a constant humidity gradient of 0.90 (relative humidity of 0.95 and 0.05 on the two sides of the test sample). 3-layer Gore-Tex is a commercially available water proof, breathable fabrics for consumer market; ePTFE membrane is the expanded polytetrafluorethylene (ePTFE) membrane with pores in the range of 200 nm, a standard reference material for breathable protective clothing; and Nylon/Cotton woven fabric is the outer fabric used in US Army protective suits.
Figure 5B:
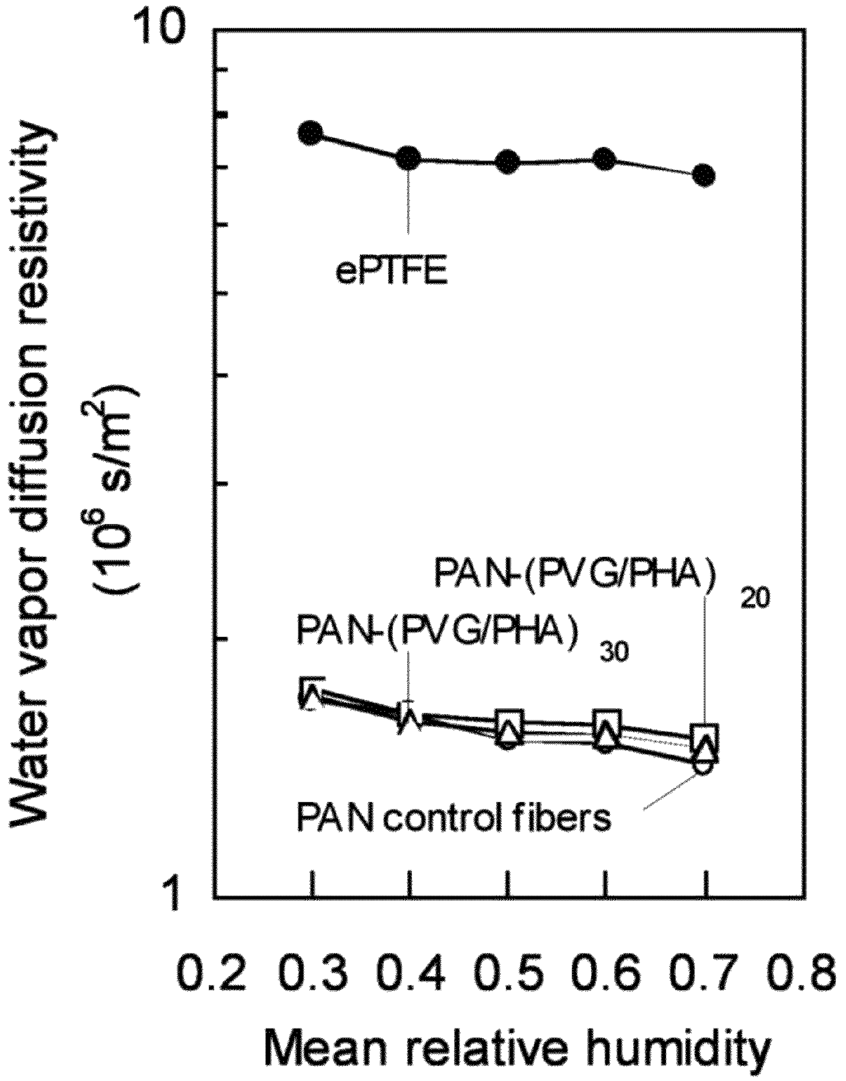
FIG. 5B depicts water vapor diffusion resistivities of (i) control and functionalized fiber mats and (ii) an expanded polytetrafluoroethylene (ePTFE) membrane with pores in the range of 200 nm, a standard reference material for breathable protective clothing. T=30° C.
Figure 6:
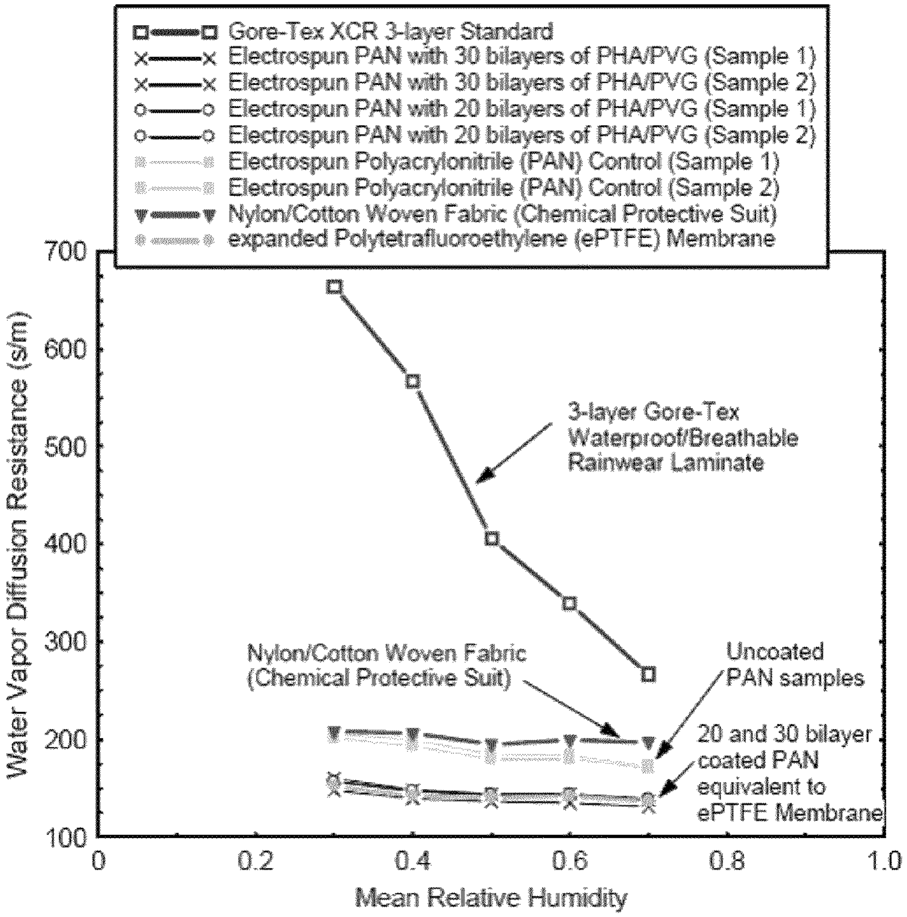
FIG. 6 depicts a graph comparing water-vapor-diffusion resistances of functionalized PAN fiber mats to reference materials.

To evaluate the transport properties of the functionalized fiber mats, the airflow resistances and water vapor diffusion resistances of these fiber mats were measured and compared to standard reference materials (FIGS. 5 and 6).

Water vapor diffusion and gas convection properties of functionalized electrospun PAN fiber mats were measured at 30° C. using an automated dynamic moisture permeation cell (DMPC) system [Gibson, P. W. J. *Coated Fabrics* 1999, 28, 300; Gibson, P. *Journal of Polymer Testing* 2000, 19, 673; and Gibson, P. W.; Rivin, D.; Kendrick, C. *International Journal of Clothing Science and Technology* 2000, 12, 96]. The test fiber sample was placed between two chambers. The sample area is about 10 $cm^2$. Air at two different relative humidities flows over the two sides of the test sample, and humidity detectors measure how much water vapor is transported through the sample. By measuring the temperature, water vapor concentration, and flow rates of the gas leaving the cell, one can determine the fluxes and resistances of gas and water vapor transported through the test sample [Gibson, P.; Schreuder-Gibson, H. L.; Rivin, D. *Colloids Surf. A* 2001, 469, 187-188].

For water vapor diffusion test, the pressure difference across the membrane was maintained zero; transport of water vapor proceeds by pure diffusion. Relative humidity on both sides of the sample increased at each set point to maintain a constant humidity gradient of 0.5, while increasing the mean relative humidity (average of the humidity on the two sides of the sample) from 0.3 to 0.7. By measuring water vapor concentrations ($C_{in}$ and $C_{out}$) and flow rates of the gas streams, one can determine the flux and the diffusion resistivity of water vapor transported through the test sample based on the following equation [Gibson, P.; Schreuder-Gibson, H. L.; Rivin, D. *Colloids Surf. A* 2001, 187, 469]:

$$N = \frac{Q(C_{out} - C_{in})}{A} = \frac{\Delta\overline{C}}{LR_{water}}$$

where N is the flux of the water vapor transported through the test sample; Q is the flow rate of the top or bottom gas stream; $C_{in}$ and $C_{out}$ are the measured inlet and outlet water vapor concentrations in either the top or the bottom gas stream; A is the area of the test sample; AC is the log mean water vapor concentration difference between top and bottom gas streams at the inlet and exit of the cell; L is the thickness of the test sample; $R_{water}$ is the water vapor diffusion resistivity. The thickness of untreated PAN fiber mats and the functionalized PAN fiber mats is 120±40 and 90±20 μm, respectively.

For airflow resistance test, constant humidity gradient of 0.90 was maintained with relative humidity of 0.95 and 0.05 on the two sides of the sample. Air pressure difference was varied systematically across the test sample to produce convective flow; then one can accordingly obtain the airflow rate through the test sample by measuring the difference between inlet and outlet airflow rate in either the top or the bottom chamber. According to Darcy's law for a porous membrane, the airflow resistivity can be determined by the following equation [Gibson, P.; Schreuder-Gibson, H. L.; Rivin, D. *Colloids Surf. A* 2001, 187, 469]:

$$R_{air} = \frac{A\Delta p}{\mu QL}$$

where $_A$ is the area of the test sample; Δp is the pressure drop through the test sample; μ is the gas dynamic viscosity; Q is the airflow rate through the membrane; L is the thickness of the test sample; $R_{air}$, the apparent airflow resistivity, is the inverse of airflow permeability.

As shown in FIG. 5A, airflow resistance of untreated electrospun PAN fiber mat is comparable to that of nylon/cotton woven fabric, which is widely used as outer fabrics in the Army chemical/biological protective suit. The functional coatings on the LbL-coated fiber mats, $(PVG/PHA)_{20}$ and $(PVG/PHA)_{30}$, cause pore size reduction by occupying the pores to some extent, consequently increasing the convective air flow resistance of electrospun fiber mats by two to three-fold (FIG. 5A).

One might expect the filling of pores reported above to affect the breathability of the fiber mats. To evaluate this potential effect, the water vapor diffusion resistivities of these fiber mats were measured and compared to standard reference material (FIG. 5B). In FIG. 5B, the LbL-functionalized fiber mats, $(PVG/PHA)_{20}$ and $(PVG/PHA)_{30}$, exhibit water vapor diffusion resistivity comparable to that of the untreated PAN fiber mats, indicating that the LbL coatings on the fibers do not affect the breathability of the fiber mats even when the surface pores are partially filled; this accords with similar observations by Krogman et al. [Krogman, K. C.; Lowery, J. L.; Zacharia, N. S.; Rutledge, G. C.; Hammond, P. T. *Nat. Mater.* 2009, 8, 512]. It also shows that the water vapor diffusion resistivities of the electrospun fibermats are lower (more breathable) than that of ePTFE membranes. The ePTFE membrane is a standard porous breathable material. Membranes that exhibit water vapor diffusion properties comparable to the ePTFE membrane are excellent candidates for utilization in breathable protective clothing. The measured airflow resistivity of the functionalized fibermats is $1.4\times10^{13}$ and $1.0\times10^{13}$ $l/m^2$ for $(PVG/PHA)_{20}$ and $(PVG/PHA)_{30}$, respectively. This effect is 4-5-fold higher than that of untreated PAN fibermats ($2.7\times10^{12}$ $l/m^2$), but 1 order of magnitude lower than that of ePTFE membrane ($1.6\times10^{14}$ $l/m^2$). This result suggests that the functional coatings occupy the pores of electrospun fiber mats to some extent, which enhances the barrier performance toward convective airflow as compared to the untreated PAN fiber mats, but such pore filling does not significantly compromise water vapor permeability. Thus, all results indicate that LbL-functionalized electrospun fibermats are highly breathable and suitable for use in protective clothing materials.

Thus, these functionalized fiber mats demonstrated better barrier performance than that of nylon/cotton woven fabrics.

Moreover, LbL-functionalized fiber mats, $(PVG/PHA)_{20}$ and $(PVG/PHA)_{30}$, have water vapor diffusion properties equivalent to the expanded polytetrafluorethylene (ePTFE) membrane (FIG. 6), which are better than that of nylon/cotton woven fabric. The ePTFE membrane is a standard porous breathable material. Membranes that achieve the water vapor diffusion properties comparable to the ePTFE membrane are excellent candidates for utilization in breathable protective clothing. However, the untreated PAN fiber mats were observed to have the higher diffusion resistance or lower water vapor transport than functionalized PAN fiber mats. The LbL electrostatic assembly involves dipping fiber mats into aqueous solution followed by drying process, resulting in the significant reduction in thickness of fiber mats, which is in accordance with the previous observations [Chen, L.; Bromberg, L.; Schreuder-Gibson, H.; Walker, J.; Hatton, T. A; Rutledge, G. C. *J. Mater. Chem.* 2009, 19, 2432]. The reduction in fiber mat thickness actually improved the breathability of the functionalized fiber mats as compared to untreated PAN mats. In addition, functional polyelectrolyte coatings on the fibers are more hydrophilic than PAN, which may further enhance the water vapor transport. The functionalized fiber mats also show far superior breathability properties to the reference Gore-Tex 3-layer laminate, which is a commercially available waterproof, breathable consumer market fabric. All results indicate that LbL-functionalized electrospun fiber mats are highly breathable, suitably used for protective clothing materials, even after the surface pores are partially filled.

DFP Degradation

Hydroxamic acid is a reactive α-nucleophile, capable of hydrolysis of organophosphate (OP) esters. Hydrolytic destruction of organophosphates (OPs) by low molecular weight hydroxamates has been established. However, until recently [Bromberg, L.; Schreuder-Gibson, H.; Creasy, W. R.; McGarvey, D. J.; Fry, R. A.; Hatton, T. A. *Ind. Eng. Chem. Res.* 2009, 48, 1650] little work has been done to study the action of polymers with hydroxamic acid groups, such as poly(N-hydroxyacrylamide) (PHA), in the degradation of OPs. The capability of PHA to decompose DFP, a common simulant for G-type nerve agents, in aqueous solution is described below.

Scheme 3. DFP degradation mediated by PHA in aqueous solution

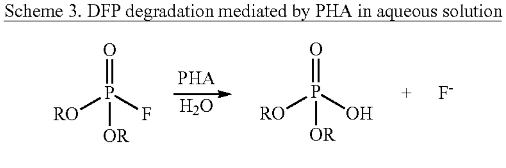

DFP

R: i-Pr

Kinetics of DFP degradation hydrolyzed by PHA in aqueous solutions were assessed by liquid state $^{31}P$ NMR spectrometry using a Varian 500 spectrometer operating at 202.46 MHz. All the experiments were conducted under conditions of excess hydroxamic acid relative to the substrate ($[HA]_o > [DFP]_o$). The reaction milieu consisted of 50 mM of TES buffer to keep solution pH constant at 7 and 20% (by volume) of deuterium oxide for signal locking The spectra were recorded at ambient temperature (25° C.) by accumulation of 64 scans. The reaction time was taken to be the midpoint of the acquisition period.

Degradation of DFP mists on PVG/PHA-functionalized fiber mats was monitored by solid state high-resolution magic angle spinning (HRMAS) $^{31}P$ NMR using a Bruker Avance 400 spectrometer (161.98 MHz for $^{31}P$) as described previously [Chen, L.; Bromberg, L.; Schreuder-Gibson, H.; Walker, J.; Hatton, T. A; Rutledge, G. C. *J. Mater. Chem.* 2009, 19, 2432]. The water content of the fiber mats, $C_w$, defined as the weight ratio of absorbed water to dry fiber mat, was maintained at 1.30 wt/wt in this work. The spectra were recorded at ambient temperature (21° C.) by accumulation of 64 scans. Triphenyl phosphate (TPP) in deuterated chloroform was used as an external reference for both liquid and solid state $^{31}P$ NMR measurements.

FIG. 1 shows a typical series of NMR spectra of DFP degradation mediated by PHA in aqueous solution as a function of time. Doublet signals at 4.6 and 9.4 ppm are attributed to the reactant, DFP, due to the splitting of the $^{31}P$ signal from the coupling of the P—F bond ($J_{P\text{-}F} \approx 970$ Hz).[51] The singlet at 16.8 ppm is assigned to the product, diisopropyl phosphate (DIP).

Degradation of DFP (Scheme 3) is mediated by PHA through the nucleophilic attack of the >N—O—H oxygen in hydroxamic acid on the pentavalent phosphorus of DFP, resulting in P—F bond cleavage and fluorine ion release.

The ratio of the relative signal integrations is proportional to the ratio of the relative concentrations of the corresponding compounds, which allows us to estimate the kinetic parameters of DFP degradation in our experiments. The time-dependent relative degree of conversion, $F_t$, was defined as:

$$F_t = \Sigma I_r / (\Sigma I_r + \Sigma I_p)$$

where $\Sigma I_r$ and $\Sigma I_p$ are the sums of the integrations of the signals corresponding to the reactant, DFP, and the product, DIP, respectively.

Figure 2:
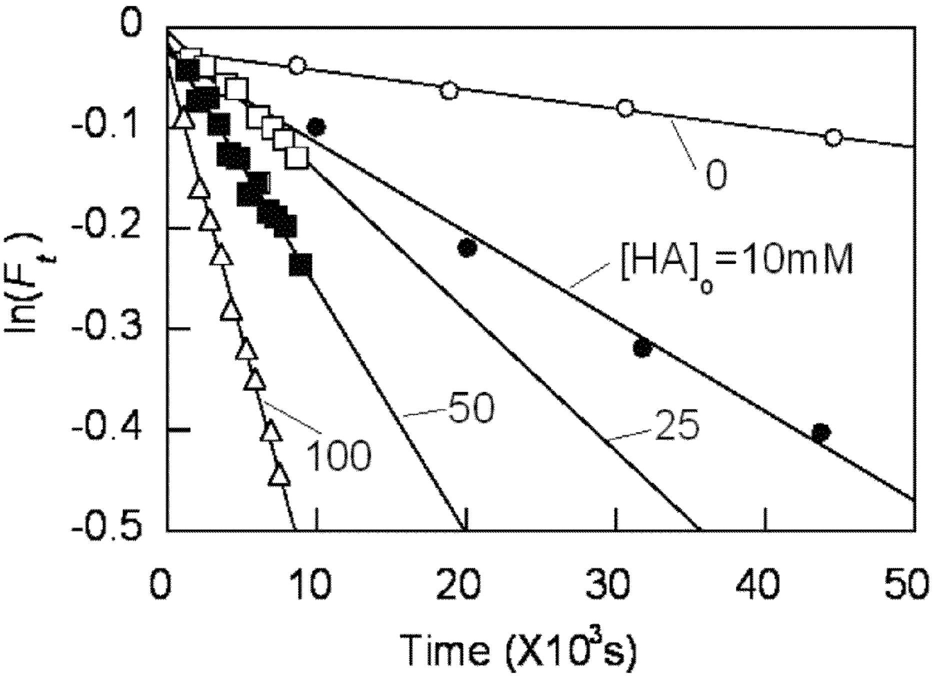
FIG. 2 depicts a graph of the kinetics of DFP hydrolysis at various initial concentrations of HA in aqueous solution. The conditions are as follows: $[DFP]_o$ is 5 mM; 50 mM TES buffer; and the pH 7.0.

FIG. 2 shows the plot of $\ln(F_t)$ vs. time for a series of experiments in which the hydroxamic acid concentration, $[HA]_o$, was varied while keeping DFP concentration constant; $[DFP]_o$ was 5 mM. All the experiments were observed to be pseudo-first order with respect to DFP, as evidenced by the linear fit of the curve $\ln(F_t)$ vs. time ($R^2 > 0.99$). The slope yields the observed reaction rate, $k_{obs}$, as described by the equation:

$$\ln(F_t) = -k_{obs} t$$

The observed rate constant without PHA ($k_{sp}$) was measured to be $1.9 \times 10^{-6}\ s^{-1}$ at pH 7.0, in accordance with previously reported values for the spontaneous hydrolysis of DFP. The observed reaction rate increases as $[HA]_o$ increases. In the case of the PHA-aided hydrolysis, the observed reaction rate consists of the PHA-aided and spontaneous reaction rate contributions:

$$r_{obs} = r_{PHA} + r_{sp} \text{ or } \frac{d[DFP]}{dt} - k_{obs}[DFP]$$
$$= -k_{PHA}[DFP] - k_{sp}[DFP]$$
$$k_{PHA} = k_2[HA]_o$$

Figure 3:
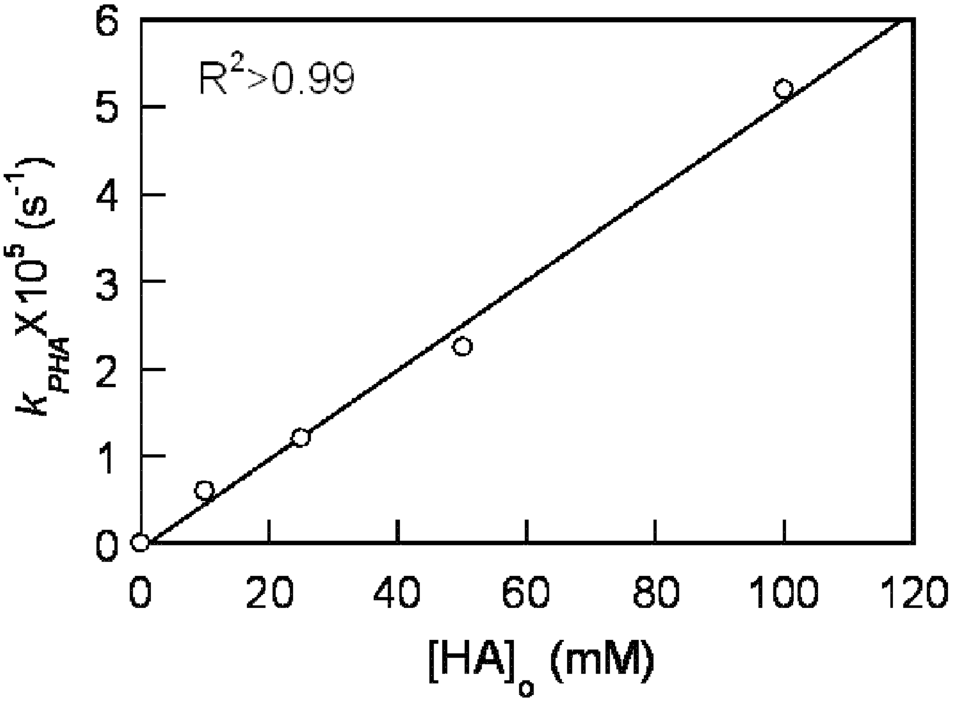
FIG. 3 depicts a graph of observed reaction constant of DFP hydrolysis versus $[HA]_o$ in aqueous solution. The conditions are as follows: $[DFP]_o$ is 5 mM; 50 mM TES buffer; the pH is 7.0; and the spontaneous hydrolysis of DFP, $k_{sp}$, is $1.9\times10^{-6}$ s$^{-1}$ at pH 7.0.

FIG. 3 shows the curve of $k_{PHA}$ vs. hydroxamic acid concentration, $[HA]_o$, in which $k_{PHA}$ is obtained by subtracting spontaneous term, $k_{sp}$, from the observed overall reaction rate, $k_{obs}$. The slope of the linear fit of this curve ($R^2 > 0.99$) yields the second order rate constant, $k_2$, which was determined to be $5.1 \times 10^{-4}\ M^{-1}\ s^{-1}$ for DFP hydrolysis mediated by PHA at pH 7.0. Given that the reaction rate is significantly affected by solution pH, the nature of the reaction medium, temperature and $pK_a$ of hydroxamic acid compounds, it is difficult to compare directly the reactivity of PHA with small molecular weight hydroxamic acid compounds. Based on the reported data, it was estimated that the second order rate constant for the DFP degradation via hydrolysis by isonicotinhydroxamic acid methiodide ($pK_a$ 7.8) in aqueous solution at pH 7.0 is in the order of $10^{-3}$ $M^{-1}$ $s^{-1}$. Therefore, the reactivity of PHA ($pK_a$ 7.5) towards DFP degradation in this study is comparable to that of isonicotinhydroxamic acid methiodide, a small molecular weight hydroxamic acid compound.

It is well known that amines and their derivatives can decompose OPs via a general base catalyzed hydrolysis. Since antimicrobial poly(N-vinyl guanidine) (PVG) is a strong polybase bearing amine groups, it can degrade DFP catalytically as well [Bromberg, L.; Hatton, T. A. *Polymer* 2007, 48, 7490]. To compare the reactivity of PVG with that of PHA, the reaction kinetics of PVG with DFP under identical conditions with the same concentration of functional groups (e.g., $[VG]_o=[HA]_o$) was conducted. The $k_{PHA}$ and $k_{PVG}$ values obtained after subtracting the spontaneous hydrolysis term were $5.5\times10^{-5}$ $s^{-1}$ and $7.7\times10^{-6}$ $s^{-1}$, respectively, at pH 7.0 with $[DFP]_o=5$ mM and $[VG]_o=[HA]_o=100$ mM. These values indicate that the reactivity of PHA towards DFP is seven-fold higher than that of PVG. Therefore, the reactivity of the PHA/PVG LbL coatings is primarily due to the presence of PHA rather than that of PVG.

Chemical Detoxification Tests

The performance of PVG/PHA functionalized fiber mats serving as chemical detoxification fabrics was tested with DFP. A DFP mist (3 μL of DFP with 7 μL of air in a 10 μL syringe) was sprayed onto the prepared fiber mat (the mass of dry fiber mat, $W_f$, was 30 mg) to mimic an attack of G-type nerve agents. The DFP degradation mediated by PVG/PHA-functionalized fiber mats was monitored by HRMAS $^{31}P$ NMR.

Figure 7:
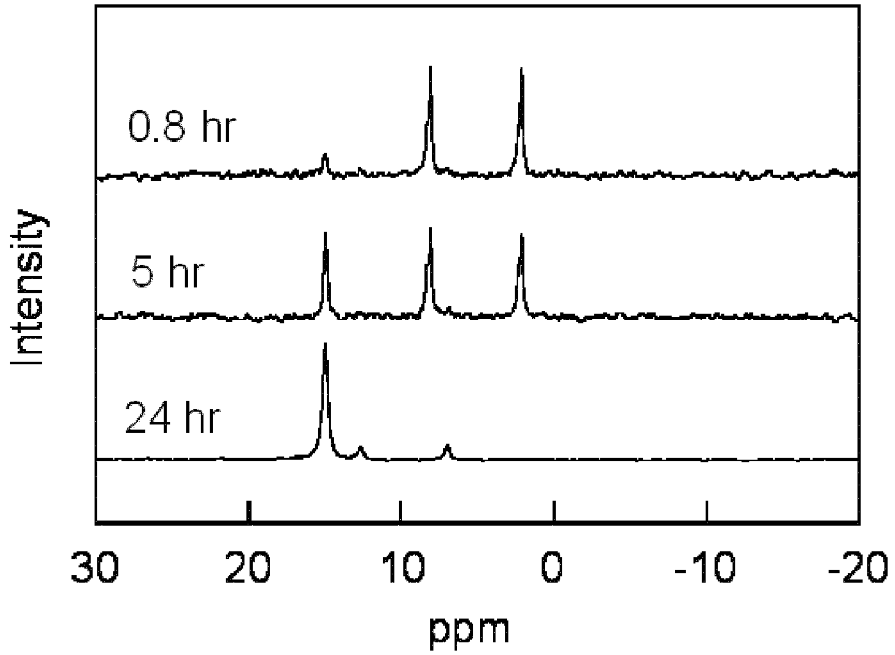
FIG. 7 depicts a time series of $^{31}$P HRMAS NMR spectra of DFP mist (3 μL) deposited onto functionalized fiber mat $(PVG/PHA)_{20}$ as a function of time. The mass of dry fiber mat, $W_f$ is 30 mg; the water content in the fiber mat, $C_w$ is 1.3 wt/wt; and $W_{DFP}$ is 3 mg.

FIG. 7 shows three representative NMR spectra of a DFP-misted fiber mat functionalized with $(PVG/PHA)_{20}$, showing decomposition as a function of time. Doublets at 3.7 and 9.7 ppm ($J_{P-F}\approx970$ Hz) are assigned to DFP. With time, the doublet peaks for DFP decreased and the singlet peak at 16.6 ppm, assigned to the product DIP, increased. The signals for the reactant and product correspond well with the NMR assessment have previously been reported. The doublets at 12.5 and 6.9 ppm observed after 24 hr are attributed to the unreacted DFP that is absorbed onto the charged polyelectrolyte coating on the fiber surfaces, which shifts the signal positions.

Figure 8:
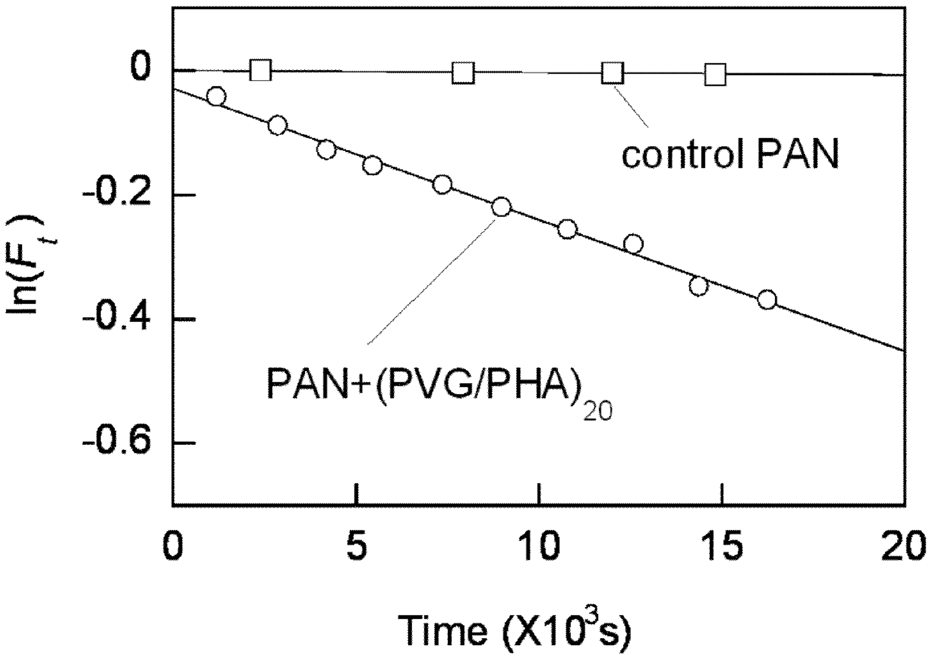
FIG. 8 depicts a graph showing the kinetics of DFP degradation in the presence of a functionalized or control fiber mat at 21° C. The mass of dry fiber mat, $W_f$, is 30 mg; the water content in the fiber mat, $C_w$ is 1.3 wt/wt; and $W_{DFP}$ is 3 mg.

FIG. 8 shows the DFP degradation kinetics on PVG/PHA-functionalized fiber mat $(PVG/PHA)_{20}$ as well as an untreated PAN control fiber mat, under identical test conditions ($W_f$, was 30 mg, $W_{DFP}$ was 3 mg, $C_w$ was 1.3 wt/wt, 21° C.). The DFP degradation mediated by the PVG/PHA-functionalized fiber mat in the presence of water was observed to be pseudo-first order with respect to DFP. The observed reaction rate is $2.1\times10^{-5}$ $s^{-1}$, which is approximately 60-fold faster than the observed spontaneous decomposition rate of DFP in the presence of the control fiber mat with the same water content. The reactivity of the functionalized fiber mats modified via the LbL electrostatic assembly method is also comparable to that for oxime-functionalized fiber mats prepared via surface oximation reported previously. The advantage of the LbL assembly method is the broader selection of available polymeric fiber substrate materials compared to the methodology of direct chemical modification of the fiber material, where the choice of material is limited to fiber-forming polymers possessing certain functional groups that can be converted to the reactive groups. The PVG/PHA-functionalized fabrics also demonstrate better reactivity towards DFP as compared to XE-555, a commonly used decontaminating, cleaning solution recommended for personal equipment.

Antibacterial Tests

The antibacterial properties of the PVG/PHA functionalized fiber mats were tested with a representative Gram-negative strain of *E. coli* and a Gram-positive strain of *S. epidermidis* using the procedure of Tiller and coworkers, with modifications [Tiller, J. C.; Liao, C.-J.; Lewis, K.; Klibanov, M. *PNAS* 2001, 98, 5981]. Specifically, the functionalized fabrics were challenged with airborne bacteria in the form of sprayed mists, to mimic combat situations, as described below.

*E. coli* (ATCC #67876) and *S. epidermidis* (ATCC #35984) were cultured overnight in LB broth and diluted in phosphate buffer solution (PBS, pH 7) to approximately $10^4$~$10^5$ cells/mL. The bacterial suspension was then sprayed onto a functionalized fiber mat (6 cm×4 cm) and a control fiber mat (6 cm×4 cm) in a fume hood using a commercial chromatography sprayer. After drying for several minutes, the fiber mats were placed on top of the growth agar plates. The plates were inverted and incubated at 37° C. for 16-20 hours. The number of viable colonies was counted visually and the reduction in the number of viable bacteria colonies was calculated after averaging three experiments.

Table 1 shows the bactericidal efficiency of the functionalized fiber mats with different levels of PVG/PHA coating.

TABLE 1

Antibacterial capability of PVG/PHA functionalized fiber mats

| | bactericidal efficiency (%) | |
|---|---|---|
| number of bilayers | *E. coli* | *S. epidermidis* |
| 1 | 20.0 | 25.0 |
| 5 | 99.5 | 99.8 |
| 10 | >99.9 | >99.9 |
| 20 | >99.9 | >99.9 |

The bactericidal action of PVG with its large positive charge density, has been attributed to its excellent capability to bind onto negatively charged cell surfaces or cytoplasmic membranes and irreversibly disrupt cell membranes, thereby killing the microorganisms [Browton, P.; Woodcock, P. M.; Heatley, F.; Gilbert, P. *J. Appl. Bacteriol.* 1984, 57, 115; Gilbert, P.; Pemberton, D.; Wilkinson, D. E. *J. Appl. Bacteriol.* 1990, 69, 585; Pemberton, D.; Wilkinson, D. E. *J. Appl. Bacteriol.* 1990, 69, 593; and Khunkitti, W.; Hann, A. C.; Lloyd, D.; Furr, J. R.; Russell, A. D. *J. Appl. Microbiol.* 1998, 84, 53]. With one bilayer coating, the fiber mat demonstrates only 20% and 25% killing efficiency, respectively, against *E. coli* and *S. epidermidis*. This low activity is due to the PVG concentration on the fiber surfaces being less than the minimum inhibitory concentration of PVG (34 μg/mL for *E. coli* and 68 μg/mL for *S. epidermidis*). As the number of bilayers increases, the killing efficiency increases significantly. In the case of five bilayer coatings, the functionalized fiber mats are capable of killing 99.8% of the viable bacteria. With ten or more bilayers functional coatings on the fiber mats, no bacterial colonies were observed on the functionalized fiber mats after the test. The effect of the last applied coating layer on the bactericidal property of PVG/PHA functionalized fiber mats has been examined. The same bactericidal efficiencies (>99.9%) were observed for functionalized fiber mats $(PVG/PHA)_{20}$ or $(PVG/PHA)_{20.5}$ and $(PVG/PHA)_{10}$ or (PVG/

PHA)$_{10.5}$ with either PHA or PVG as a last applied coating layer in electrostatic assembly. This can be attributed to interpenetration between neighboring layers or interlayer diffusion of polyelectrolytes, resulting in the presence of PVG in the outer layer of functional coatings on fiber surfaces.[62-64] A disk diffusion (Kirby Bauer) test was conducted on functionalized fiber mat (PVG/PHA)$_{20}$ to test for possible release of PVG from the functional coatings to the surrounding environments. No zone of inhibition was observed for the fiber mat after the test, indicating that functional PVG/PHA coatings on fiber surfaces do not release PVG out to the proximity under test conditions, and only kill bacteria on contact.

Simulation of Reactive Fiber Systems

All the previous work demonstrated that lightweight breathable reactive and/or bactericidal electrospun fiber mats can be fabricated by various methods. These functionalized fiber mats could be incorporated into next generation of protective clothing system as key reactive layer(s). Although the good performance of these functionalized fiber mats to detoxify representative chemical and biological toxins have been illustrated, the function of self-detoxifying protective fabrics containing these functional mats as a reactive barrier against chemical warfare agents in combat situations remains unanswered. However, given the acute toxicity of organophosphate chemical warfare agents and limited facility, it was not possible to conduct experiments to test the performance of these new self-detoxifying protective fabrics. Instead, herein is disclosed simulations of the reactive protective fabric systems to provide insights on the performance of these reactive fiber systems, which could guide further design of new protective clothing.

Figure 9:
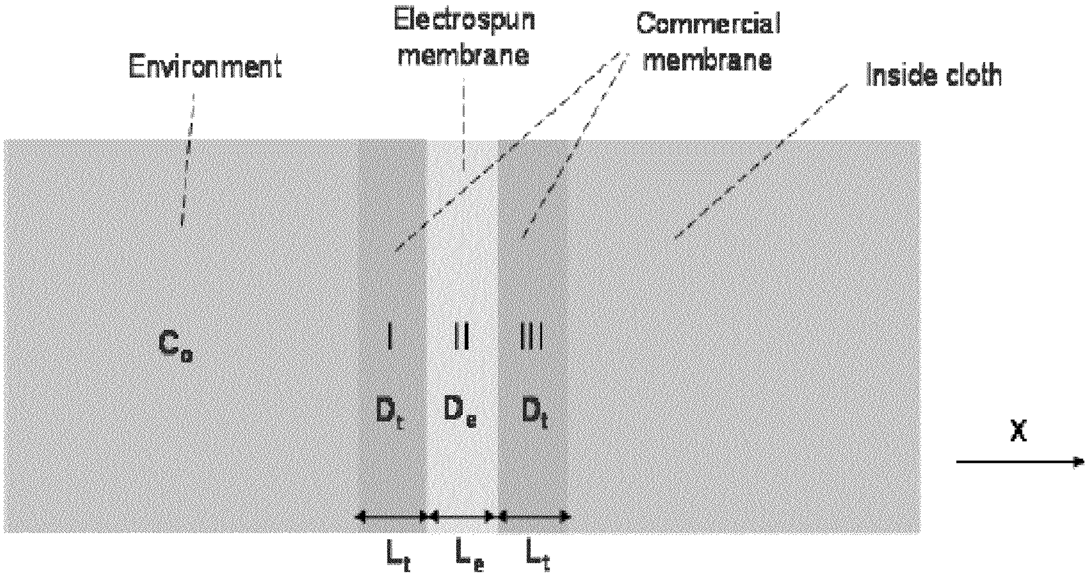
FIG. 9 depicts a schematic diagram of the reactive fiber system.

FIG. 9 shows a schematic picture of 1-D reactive fiber system. One reactive electrospun fiber mat is placed between two identical commercial fabrics. Herein is considered the worst case with toxic chemical agent in the environment in its vapor state since liquid toxin will diffuse through fabrics system much more slowly than vaporous toxin. We assume the concentration of vaporous toxin constant ($C_o$) in the environment. Then the concentration of toxin inside clothing system is monitored as a function of time. To simplify the problem, only the diffusion of toxin through the reactive fiber system was considered, neglecting the convective transport of toxins through the system. In commercial membrane region, I and III, only diffusion of toxins occurs. However, in reactive electrospun membrane region, II, both diffusion of toxins and reaction with toxins exist. The dimensionless governing equations for these regions are described as follows:

$$\text{II: } \frac{\partial \theta}{\partial \tau} = \frac{\partial^2 \theta}{\partial \eta^2} - Da\theta$$

$$\text{I and III: } \frac{\partial \theta}{\partial t} = \frac{D_t}{D_e}\frac{\partial^2 \theta}{\partial \eta^2}$$

$$\theta = \frac{C}{C_0}$$

$$\eta = \frac{x}{L}$$

$$\tau = \frac{t}{t_D}$$

$$t_D = \frac{L^2}{D_e}$$

$$Da = \frac{kL^2}{D_e}$$

where C is concentration; x is length along x axis; t is time; $D_e$ is diffusivity of toxin in electrospun membrane; $D_t$ is diffusivity in commercial membrane; k is first-order reaction constant; L is characteristic length scale; $t_D$ is characteristic time scale; $D_a$ is a dimensionless number to characterize the ratio of reaction rate vs. diffusion rate; θ, η, τ is dimensionless concentration, length and time, respectively. Based on previous water vapor diffusion resistance measurements, the diffusivity of water vapor through the functionalized fiber mats is estimated to be $10^{-7}$-$10^{-8}$ $m^2/s$. Considering organophosphates are larger than water, diffusivity $D_e$ for organophosphates is estimated to be in the order of $10^{-8}$ $m^2/s$. Assume L=1 mm, the reaction constant k is estimated to be in the order of $10^{-3}$ $s^{-1}$ according to our previously reported reactivity results. In this regard, $D_a$ is in the order of 0.1. Characteristic time scale, $t_D$, through L is 100 s. It has been reported that $D_t/D_e$ is in the order of 0.01 [Gibson, P.; Schreuder-Gibson, H.; Rivin, D. *Colloids Surf. A* 2001, 187-188, 469].

Figure 10:
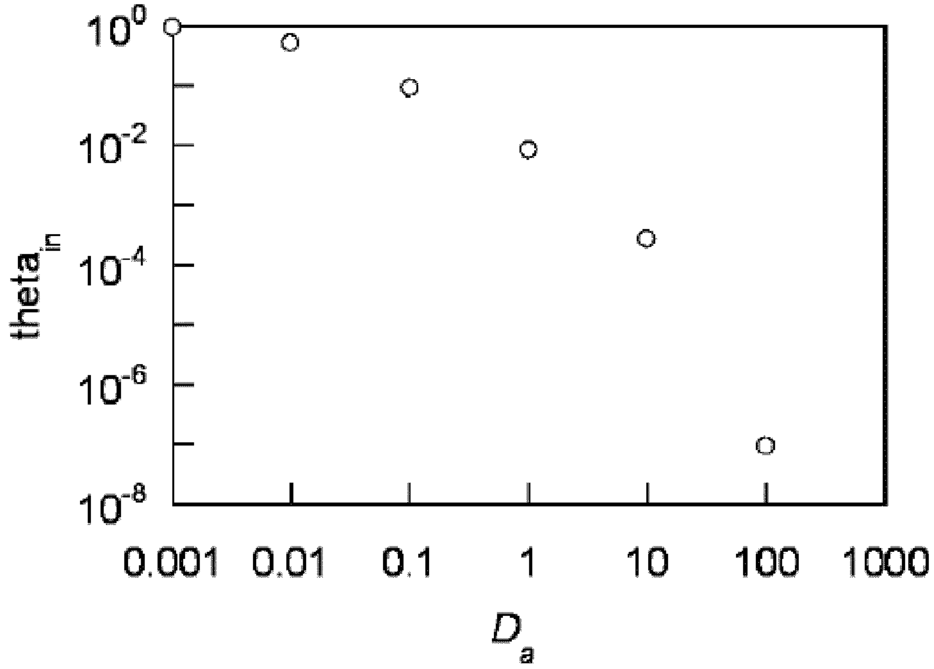
FIG. 10 depicts $\theta_{in}$ vs. $D_a$ at steady state. $D_t/D_e=0.01$; $L_e=L_t=L=1$ mm. $\theta_{in}$: dimensionless concentration θ inside cloth.
Figure 11:
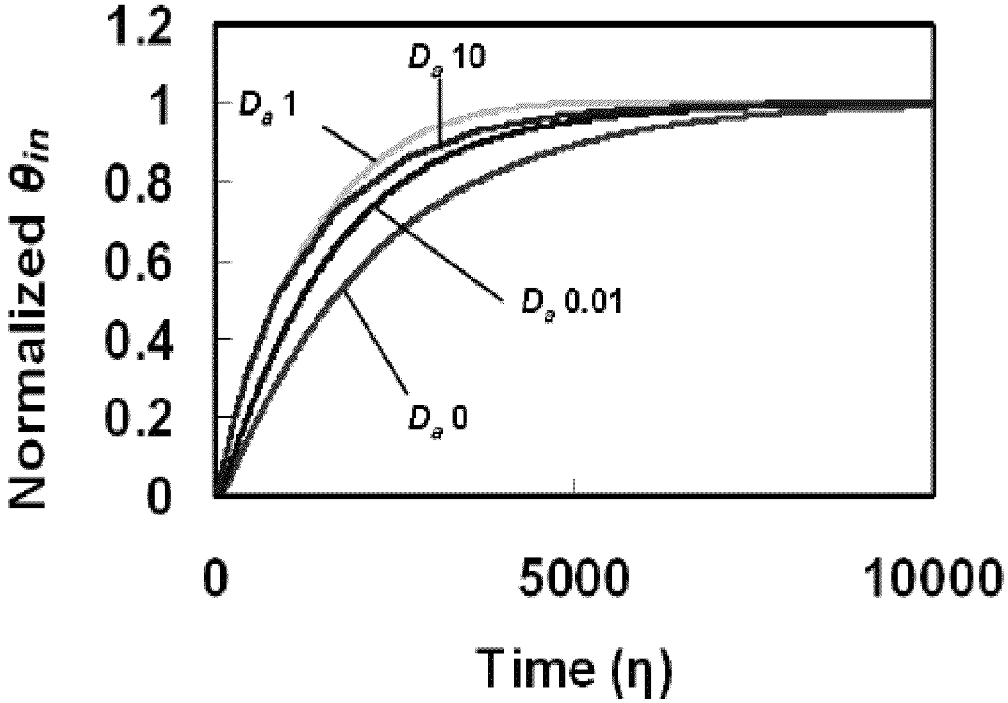
FIG. 11 depicts normalized $\theta_{in}$ vs. time for various $D_a$. Normalized $\theta_m$: dimensionless concentration θ inside cloth, normalized by steady state value.

All numerical simulation work was performed using commercial Comsol Multiphysics® software. FIG. 10 shows dimensionless concentration of toxins inside cloth as a function of $D_a$ at steady state. When dimensionless concentration is normalized by its steady state value (FIG. 11), it was observed that the time scales to steady state for all cases of $D_a$ are very similar (5000 $t_D$), which is attributed to the constant thicknesses ($L_e$, $L_t$) of membranes in the system. Therefore, the reaction (or contact) time with reactive electrospun membrane is constant in these situations. As $D_a$ increases, the reactivity (k) of functionalized electrospun fiber mats increases, leading to the consumption of more toxins at the same reaction time. It results in the significant decrease in toxin concentration ($\theta_{in}$) inside cloth (FIG. 10). At $D_a$=0.1, which is a typical value representing previously reported reactive fiber mats, the steady state toxin concentration inside cloth is 8.9% of the toxin concentration ($C_o$) in the environment. The time scale to steady state is $5\times10^5$ s, corresponding to 140 hour. Depending on the absolute value of toxin concentration, $C_o$, in the environment along with the known lethal dosage of toxins, one may estimate the valid protection time for the reactive protective fabric system.

Figure 12:
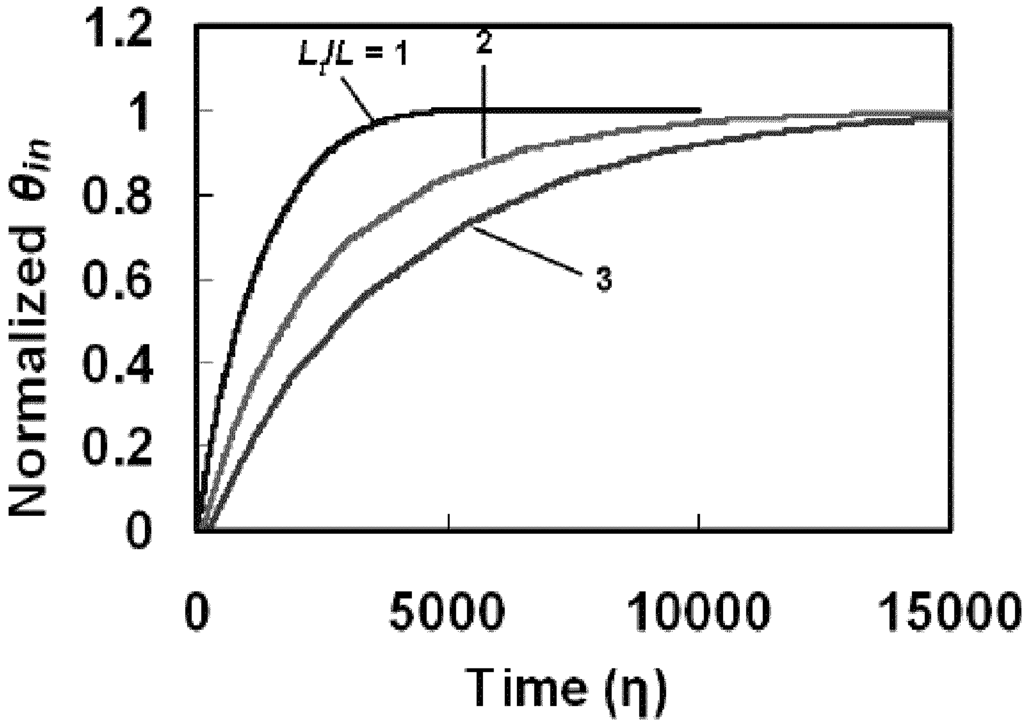
FIG. 12 depicts normalized $\theta_{in}$ vs. time for various $L_t/L$, $L_e/L=1$; $D_a=1$; Normalized $\theta_{in}$: dimensionless concentration θ inside cloth, normalized by steady state value.
Figure 13:
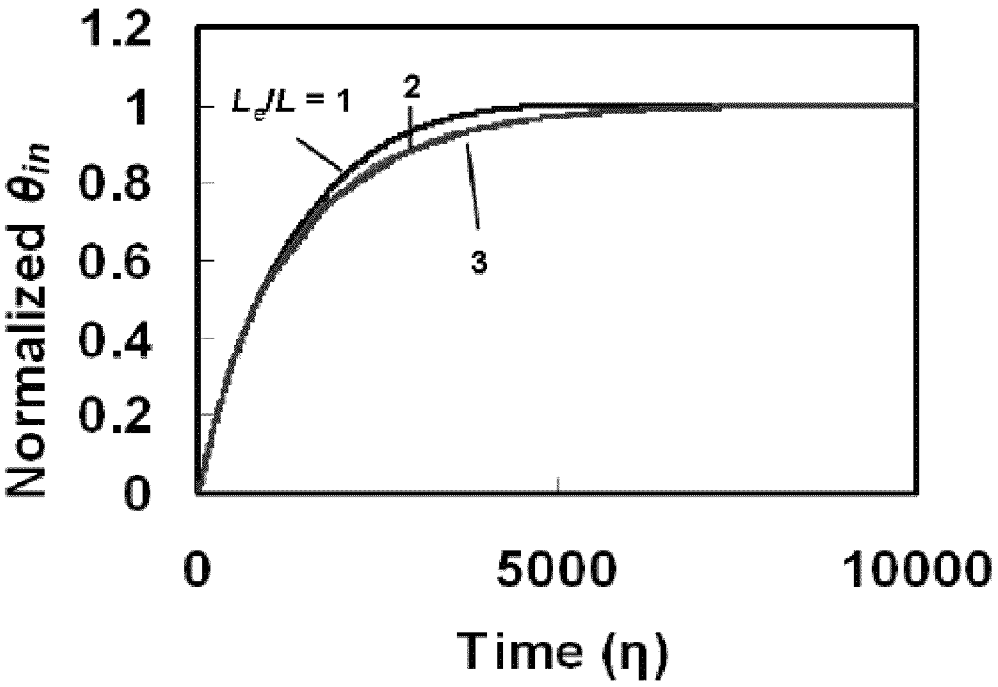
FIG. 13 depicts Normalized $\theta_{in}$ vs. time for various $L_e/L$, $L_t/L=1$; $D_a=1$; Normalized $\theta_{in}$: dimensionless concentration $\theta$ inside cloth, normalized by steady state value.
Figure 14:
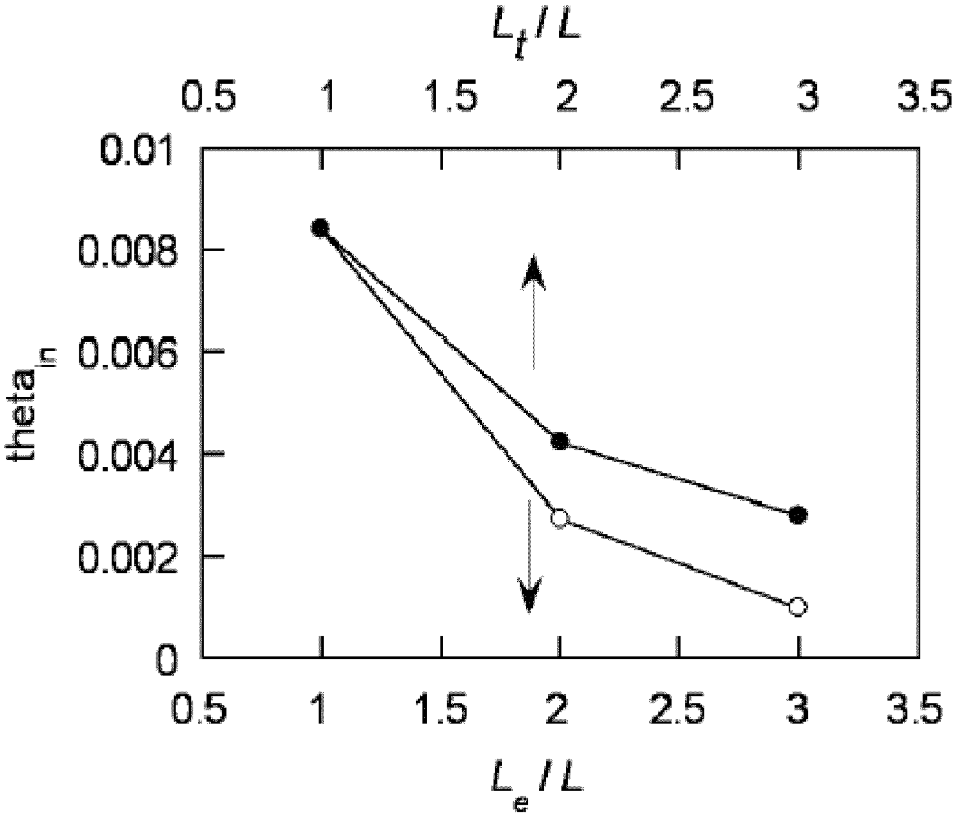
FIG. 14 depicts $\theta i_n$ vs. Lt/L at Le/L=1. $\theta_{in}$ vs. $L_e/L$ at $L_t/L=1$. $D_t/D_e=0.01$; $D_a=1$.

Several simulations to evaluate the effect of the thickness of reactive fiber system on the performance were also conducted. FIG. 12 shows curves of the normalized $\theta_{in}$ vs. time as a function of $L_t$, the thickness of commercial fabric, when $L_e$, the thickness of reactive electrospun membrane, is fixed. The increase in $L_t$ leads to the corresponding increase in time scale to the steady state. 13 shows the curves of normalized $\theta_{in}$ vs. time as a function of $L_e$ when $L_t$ is kept constant. The time scale remains approximately constant when $L_e$ is varied and $L_t$ is kept constant. These results indicated the diffusion through the commercial membrane is the rate-determine step in reaching the steady state. This can be explained by two orders of magnitude smaller of diffusivity in commercial membrane, $D_t$, compared to diffusivity in reactive electrospun membrane, $D_e$. We further compare steady state $\theta_{in}$ in these two series of experiments. Interestingly, Le has a larger effect on steady state $\theta_{in}$ than $L_t$. An increase in $L_e$ results in more reduction in steady state $\theta_{in}$ compared to that for Lt (FIG. 14). In fact increasing $L_e$ leads to longer reaction or contact time of toxins with reactive electrospun membrane, which allows for detoxification of more toxins and results in the reduction in steady state $\theta_{in}$. On the other hand, in term of increasing $L_t$ while maintaining $L_e$ constant, the reaction or contact time with reactive electrospun membrane remains constant; the diffusion resistance in commercial membrane significantly increases as $L_t$ increases, causing an increase in toxin concentration in reactive electrospun membrane. Consequently, more toxins are decomposed since reaction rate is essentially determined by kθ. In this regard, by manipulating the thicknesses of these composite membranes, the transport properties and reactivity of these self-detoxifying protective clothing could be tuned.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed in this application.

We claim:

1. A membrane comprising a plurality of polymer-coated electroprocessed nanofibers, wherein said polymer coating comprises at least one polyelectrolyte bilayer, said bilayer comprises a plurality of polycations in a polycationic layer and a plurality of polyanions in a polyanionic layer, at least one of said polycations is antimicrobial, at least one of said polyanions is esterolytic toward phosphate esters, and said membrane is both antimicrobial and esterolytic.

2. The membrane of claim 1, wherein the electroprocessed nanofibers are electrospun.

3. The membrane of claim 1, wherein the electroprocessed nanofibers are homopolymers, copolymers, or a blend of polymers, selected from the group consisting of alginates, aromatic copolyesters, cellulose acetates, cellulose nitrites, collagens, ethylene-methacrylic acid copolymers, ethylene-vinyl acetate copolymers, fluoropolymers, modified celluloses, neoprenes, polyp-xylylene), polyacrylamides, polyacrylates, polyacrylonitriles, polyamides, polyarylamides, polyarylenevinylenes, polybenzimidazoles, polybenzothiazoles, polybutadienes, polybutenes, polycarbonates, polyesters, polyether ketones, polyethers, polyethylenes, polyhydroxyethyl methacrylates, polyimides, polylactides, polylactones, polymethacrylates, polymethacrylonitriles, polymethylmethacrylates, poly-N-vinylpyrrolidones, polyolefins, polyoxazoles, polyphenylene, polypropylenes, polysilanes, polysiloxanes, polystyrenes, polysulfides, polysulfones, polytetrafluoroethylenes, polyurethanes, polyvinyl acetates, polyvinylacetate-methacrylic copolymers, polyvinylidene chlorides and unmodified celluloses.

4. The membrane of claim 1, wherein at least one polycation of said plurality of polycations inhibits the growth of bacteria on contact.

5. The membrane of claim 1, wherein at least one polycation of said plurality of polycations is a polymer comprising at least one subunit represented by

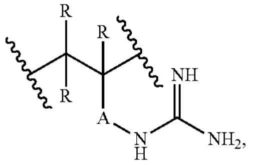

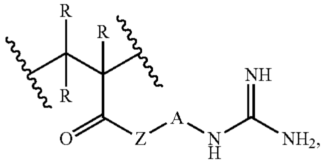

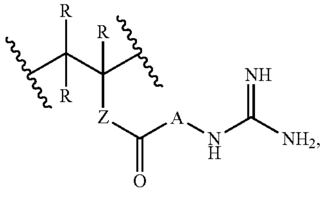

-continued

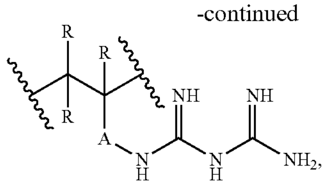

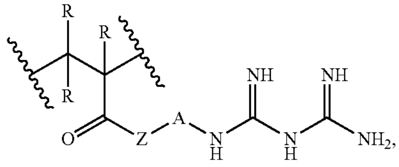

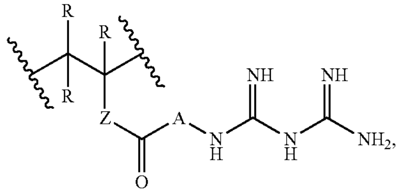

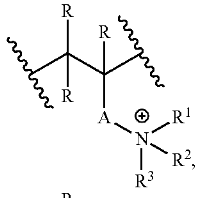

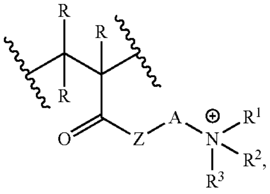

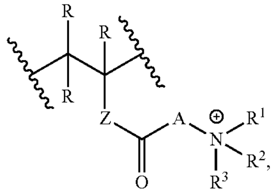

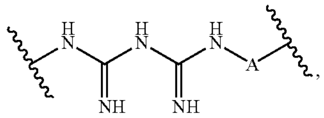

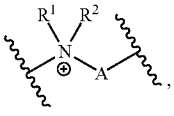

or salts thereof;

wherein, independently for each occurrence,

Z is absent, —O—, —S—, or —N(R)—;

A is absent or selected from the group consisting of alkylene, arylene, heteroarylene, alkylene-arylene, alkylene-heteroarylene, arylene-alkylene, heteroarylene-alkylene, alkylene-arylene-alkylene, and alkylene-heteroarylene-alkylene;

R is hydrogen or alkyl;

$R^1$ is hydrogen or alkyl;

$R^2$ is alkyl; and $R^3$ is alkyl.

6. The membrane of claim 5, wherein the at least one polycation is a polymer comprising at least one subunit represented by

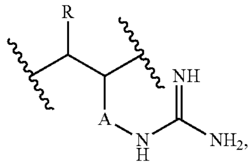

-continued

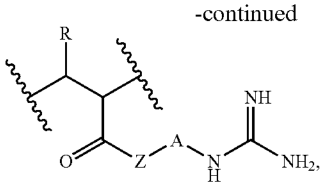

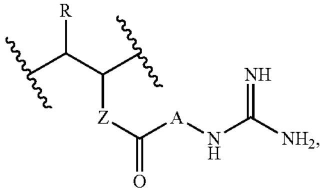

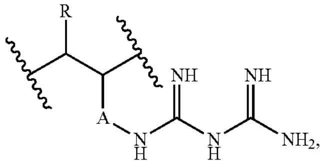

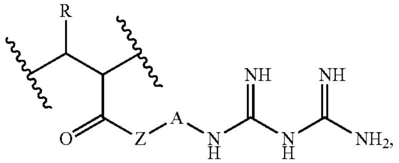

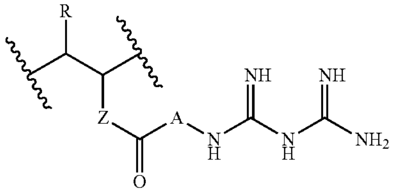

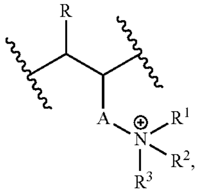

or

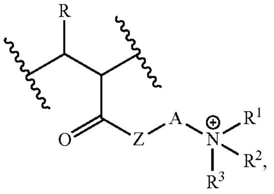

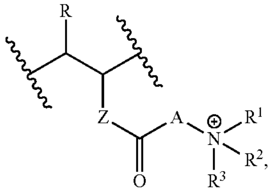

or salts thereof.

7. The membrane of claim 5, wherein the at least one polycation is a polymer comprising at least one subunit represented by

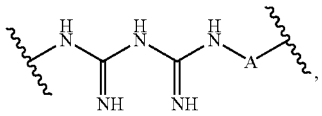

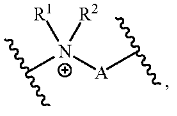

or a salt thereof.

8. The membrane of claim 1, wherein said plurality of polycations consists essentially of poly(N-vinylguanidine) (PVG), poly(diallyl dimethyl ammonium chloride) (PDAC), polyarginine, polyallylaminehydrochloride (PAH), linear polyethyleneimine (LPEI), branched polyethyleneimine (BPEI), poly(amidoamine) dendrimer (PAMAM), poly(N-(1,3-bis(2-ethylhexyl)-5-methylhexahydropyrimidin-5-yl)

acrylamide), poly(hexamethylenebiguanide) (PHMB), or poly(hexamethylene-5-(phenylene)biguanide, or salts thereof.

9. The membrane of claim 1, wherein said plurality of polycations consists essentially of poly(N-vinylguanidine) (PVG) or a salt thereof.

10. The membrane of claim 1, wherein at least one polyanion of said plurality of polyanions degrades organophosphorus esters on contact.

11. The membrane of claim 1, wherein at least one polyanion of said plurality of polyanions is a polymer comprising at least one subunit represented by

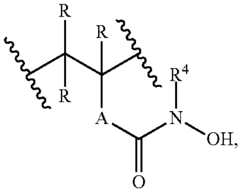

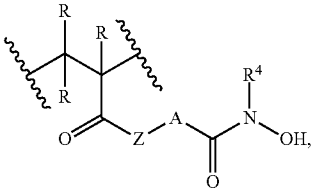

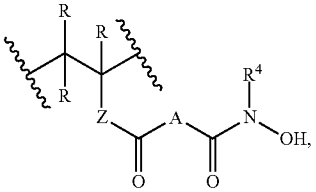

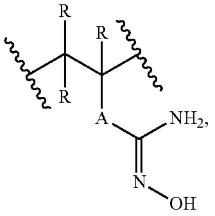

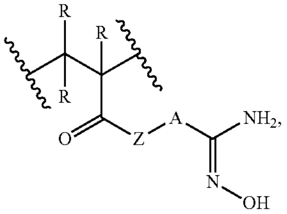

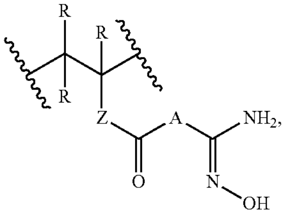

and salts thereof;

wherein, independently for each occurrence,

Z is —O—, —S—, or —N(R)—;

A is absent or selected from the group consisting of alkylene, arylene, heteroarylene, alkylene-arylene, alkylene-heteroarylene, arylene-alkylene, heteroarylene-alkylene, alkylene-arylene-alkylene, and alkylene-heteroarylene-alkylene;

R is hydrogen or alkyl; and $R^4$ is hydrogen or alkyl.

12. The membrane of claim 11, wherein the at least one polyanion is a polymer comprising at least one subunit represented by

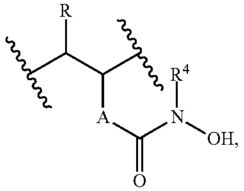

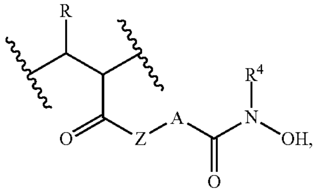

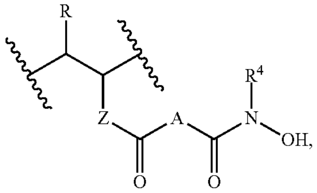

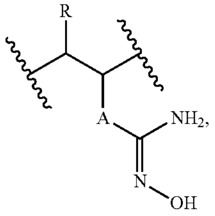

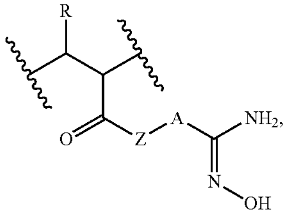

-continued

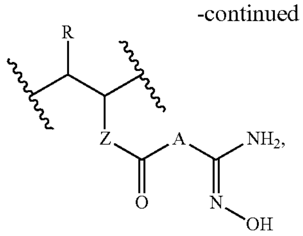

and salts thereof.

13. The membrane of claim 1, wherein said plurality of polyanions consists essentially of poly(N-hydroxyacrylamide) (PHA), poly(N-hydroxyacrylamidoxamate), poly(octanedioic acid hydroxyamide ispropenylamide), poly(2-ethyl-2-hexyl-hex-5-enoic acid hydroxyamide), poly(N-[(hydroxy-methyl-carbamoyl)-methyl]-2-methyl-acrylamide), or salts thereof.

14. The membrane of claim 1, wherein said plurality of polyanions consists essentially of poly(N-hydroxyacrylamide) (PHA) or a salt thereof.

15. The membrane of claim 1, wherein the polymer coating is conformal.

16. The membrane of claim 1, wherein the air flow resistivity of the membrane is between about $1.0\times10^{13}$ $l/m^2$ to about $1.4\times10^{13}$ $l/m^2$.

17. The membrane of claim 1, wherein the water vapor diffusion resistivity of the membrane is between about $1\times10^6$ $s/m^2$ to about $2\times10^6$ $s/m^2$ at a relative humidity of between about 0.3 and 0.7.

18. An article comprising a membrane of claim 1.

19. The article of claim 18, wherein the article is a fabric, filter, mask, or article of clothing.

20. The membrane of claim 1, wherein said plurality of polycations consists essentially of poly(N-vinylguanidine) (PVG) or a salt thereof; and said plurality of polyanions consists essentially of poly(N-hydroxyacrylamide) (PHA) or a salt thereof.

* * * * *